United States Patent [19]
Terada et al.

[11] Patent Number: 5,571,914
[45] Date of Patent: Nov. 5, 1996

[54] 4-DESOXY-4-EPIPODOPHYLLOTOXIN DERIVATIVE OR PHARMACEUTICALLY ACCEPTABLE SALT THEREOF

[75] Inventors: Tadafumi Terada, Saitama; Katsuhiko Fujimoto, Honjo; Makoto Nomura; Junichi Yamashita, both of Hannou; Setsuo Takeda, Tokushima; Takashi Kobunai, Naruto; Hideo Yamaguchi, Kawanishi; Konstanty Wierzba, Saitama, all of Japan

[73] Assignee: Taiho Pharmaceutical Co. Ltd., Tokyo, Japan

[21] Appl. No.: 466,733

[22] Filed: Jun. 6, 1995

Related U.S. Application Data

[62] Division of Ser. No. 375,565, Jan. 13, 1995, Pat. No. 5,489,698, which is a continuation of Ser. No. 924,079, filed as PCT/JP92/00051, Jan. 22, 1992, abandoned.

[30] Foreign Application Priority Data

Jan. 25, 1991 [JP] Japan ............................... 3-87140
Mar. 26, 1991 [JP] Japan ............................... 3-61706
Apr. 22, 1991 [JP] Japan ............................... 3-90794

[51] Int. Cl.⁶ .................. C07D 413/00; C07D 407/00
[52] U.S. Cl. ............... 544/148; 544/375; 546/187; 546/197; 546/14; 546/283.7; 548/526; 549/298
[58] Field of Search .................. 549/298; 546/187, 546/197, 270; 544/148, 375; 548/526

[56] References Cited

FOREIGN PATENT DOCUMENTS 61-103883 5/1986 Japan.
63-10789 1/1988 Japan.
2-191279 7/1990 Japan.

OTHER PUBLICATIONS

Podophyllotoxin Analogs: effects on DNA Topoisomerase II, Tubulin Polymerization, Human Tumor Kb Cells, and Their VP–16–Resistant Varients (1989).
Chemical Abstracts, vol. 112, No. 1, 1 Jan. 1990, JP–A–1 117 885.
Chemical Abstracts, Vo. 115, No. 19, 11 Nov. 1991, JP–A–3 127 792.

*Primary Examiner*—C. Warren Ivy
*Assistant Examiner*—Amelia Owens
*Attorney, Agent, or Firm*—Nikaido, Marmelstein, Murray & Oram LLP

[57] ABSTRACT

A 4-desoxy-4-epipodophyllotoxin derivative of the following formula

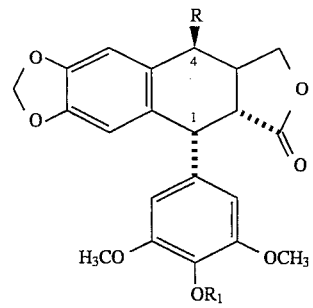

wherein R and $R_1$ are as defined in the specification or a pharmaceutically acceptable salt thereof as well as an antitumor composition comprising such derivative or salt as an active ingredient.

3 Claims, No Drawings

4-DESOXY-4-EPIPODOPHYLLOTOXIN DERIVATIVE OR PHARMACEUTICALLY ACCEPTABLE SALT THEREOF

This is a division of application Ser. No. 08/375,565, filed Jan. 13, 1995, now U.S. Pat. No. 3,489,698, which is a continuation of application Ser. No. 07/924,079, filed as PCT/JP92/00051, Jan. 22, 1992, now abandoned.

TECHNICAL FIELD

The present invention relates to novel 4-desoxy-4-epipodophyllotoxin derivatives and pharmaceutically acceptable salts thereof which have antitumor activity and are of use as antitumor agents.

BACKGROUND ART

Podophyllotoxin derivatives having antitumor activity have long been known and etoposide and teniposide are among them. However, these compounds may cause serious adverse reactions including leukopenia, thrombopenia, alopecia, nausea and vomiting so that they cannot be clinically put to use with insured safety. Thus, no satisfactory compounds has been discovered as yet.

DISCLOSURE OF THE INVENTION

Noting these problems of the prior art, the inventor of the present invention explored this field of technology with enthusiasm and found that a novel 4-desoxy-4-epipodophyllotoxin derivative of the following general formula (I) or a pharmaceutically acceptable salt thereof has very strong antitumor activity and is useful as an antitumor agent. The finding has led to the present invention.

Thus, the present invention provides a 4-desoxy-4-epipodophyllotoxin derivative of the general formula (I):

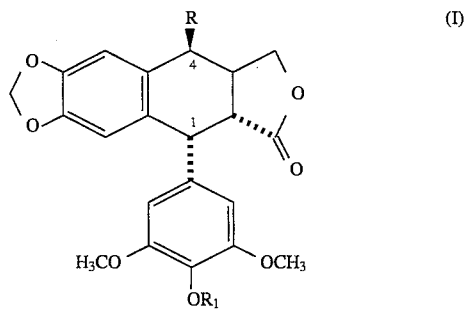

(I)

wherein $R_1$ is a hydrogen atom, a methyl group, a benzyloxycarbonyl group, a lower alkanoyl group which may have one or more halogen atoms or a group of the formula —Si(Rx)(Ry)(Rz) (where Rx, Ry and Rz are the same or different and each is a lower alkyl group or a phenyl group); R is a lower alkenyl group, a lower alkyl group having at least one hydroxyl group, a group of the formula —$(CH_2)_m$CHO (where m is an integer of 0 to 4) a lower alkyl group having a ketoaldehyde group or a group of the formula —$(CH_2)_n NR_2 R_3$ (where n is an integer of 1 to 6); $R_2$ and $R_3$ are the same or different and each is a hydrogen atom, a cycloalkyl group, a group of the formula —N(Ra)(Rb) (where Ra and Rb are the same or different and each is a lower alkyl group or a phenyl group or Ra and Rb may combine to form a lower alkyl-substituted piperazino group) or a lower alkyl group which may be substituted by hydroxy, lower alkoxy, phenyl, 6-membered nitrogen-containing heterocyclic group or a group of the formula —N(Rc)(Rd) (where Rc and Rd are the same or different and each is a lower alkyl group); $R_2$ and $R_3$ may combine to form a cyclic structure which may optionally include additional oxygen and/or nitrogen atoms and may further have a lower alkyl which may be substituted by hydroxy, or piperidino group, as a substituent; provided, however, that where $R_1$ is a hydrogen atom, R is —$(CH_2)_m$CHO or —$(CH_2)_n NR_2 R_3$, or a pharmaceutically acceptable salt thereof.

The compound of general formula (I) according to the present invention has excellent antitumor activity and is effective in the treatment of various tumors.

Therefore, the invention provides an antitumor composition comprising an effective amount of a compound of the above general formula (I) or a pharmaceutically acceptable salt thereof and a pharmaceutically acceptable carrier.

The present invention further provides a method of treating tumors in mammalian animals which comprises administering a compound of the above general formula (I) or a pharmaceutically acceptable salt thereof to mammalian animals.

Referring to the above general formula (I), the lower alkanoyl group $R_1$ includes straight-chain or branched-chain $C_{2-5}$ alkanoyl groups such as acetyl, propionyl, butyryl, isobutyryl, valeryl, isovaleryl, pivaloyl, etc. and the halogen atom may for example be fluorine, chlorine, bromine or iodine. The lower alkyl group, as designated by Rx, Ry, Rz, $R_2$, $R_3$, Ra, Rb, Rc and Rd, includes straight-chain or branched-chain $C_{1-6}$ alkyl groups such as methyl, ethyl, n-propyl, isopropyl, n-butyl, isobutyl, sec-butyl, tert-butyl, pentyl, neopentyl, hexyl and so on. The lower alkenyl group R includes straight-chain or branched-chain $C_{2-6}$ alkenyl groups such as vinyl, 1-propenyl, isopropenyl, allyl, 2-butenyl, 2-methyl-2-butenyl, 3-pentenyl, 4-hexenyl and so on. The lower alkyl group having a hydroxy group includes straight-chain or branched-chain $C_{1-6}$ alkyl groups having 1 or 2 hydroxyl groups, such as hydroxymethyl, 2-hydroxyethyl, 2-hydroxypropyl, 3-hydroxypropyl, 2,3-dihydroxypropyl, 2,3-dihydroxybutyl, 2,3-dihydroxypentyl, 2,3-dihydroxyhexyl and so on. The lower alkyl group having a ketoaldehyde group includes $C_{1-6}$ alkyl groups having an α- or β-ketoaldehyde group, such as 2-oxo-2-formyl-1-ethyl, 2-oxo-3-formyl-1-propyl, 3-oxo-3-formyl-1-propyl, 3-oxo-4-formyl-1-butyl and so on.

Referring, further, to the above general formula (I), the lower alkoxy group as represented by $R_2$ and $R_3$ includes straight-chain or branched-chain $C_{1-6}$ alkoxy groups such as methoxy, ethoxy, n-propoxy, iso-propoxy, n-butoxy, isobutoxy, sec-butoxy, tert-butoxy, pentyloxy, hexyloxy and so on. The cycloalkyl group includes $C_{1-6}$ cycloalkyl groups such as cyclopropyl, cyclobutyl, cyclopentyl, cyclohexyl and so on. The 6-membered nitrogen-containing heterocyclic group includes such heterocyclic groups as pyridyl, piperidino, morpholino and so on. The cyclic structure which $R_2$ and $R_3$ may combinedly form and which may further contain additional oxygen and/or nitrogen atoms includes pyrrolidine, piperidine, morpholine, piperazine and so on.

The pharmaceutically acceptable salt of 4-desoxy-4-epipodophyllotoxin derivative according to the present invention includes the corresponding salts of various organic acids such as formic acid, acetic acid, propionic acid, trifluoroacetic acid, tartaric acid, malic acid, maleic acid, fumaric acid, succinic acid, oxalic acid, etc. and of various inorganic acids such as hydrochloric acid, hydrobromic acid, sulfuric acid, phosphoric acid and so on.

The preferred species of the compound of general formula (I) are compounds in which $R_1$ is a hydrogen atom or a benzyloxycarbonyl group and R is a group of the formula —$(C_2)_n NR_2 R_3$.

The most desirable species are compounds in which $R_1$ is a hydrogen atom and R is a group of the formula $(CH_2)_n NR_2 R_3$ wherein n is 2 or 3; $R_2$ and $R_3$ are the same or different and each is a hydrogen atom, a group of the formula —N(Ra)(Rb) (where Ra and Rb are the same or different and each is a lower alkyl group or Ra and Rb may combine to form a lower alkyl-substituted piperazino group) or a lower alkyl-group which may be substituted by a 6-membered nitrogen-containing heterocyclic group or a group of the formula —N(Rc)(Rd) (where Rc and Rd are the same or different and each is a lower alkyl group); or $R_2$ and $R_3$ may combine to form a cyclic structure which may include additional oxygen and/or nitrogen atoms and be substituted by a lower alkyl or piperidino group.

The compound of general formula (I) according to the present invention can be produced in accordance with the following reaction scheme 1, for instance.

<Reaction scheme 1>

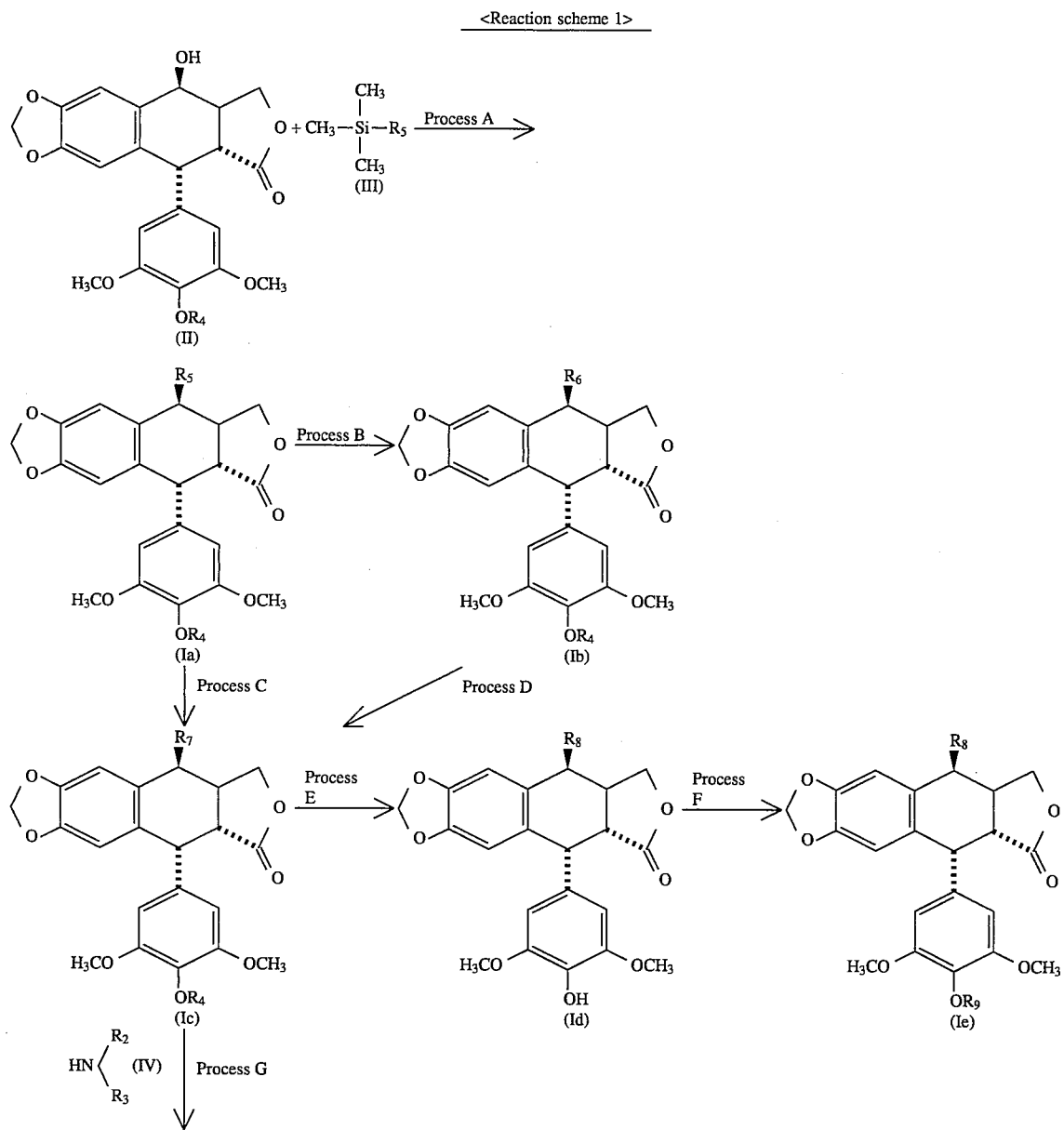

<Reaction scheme 1>

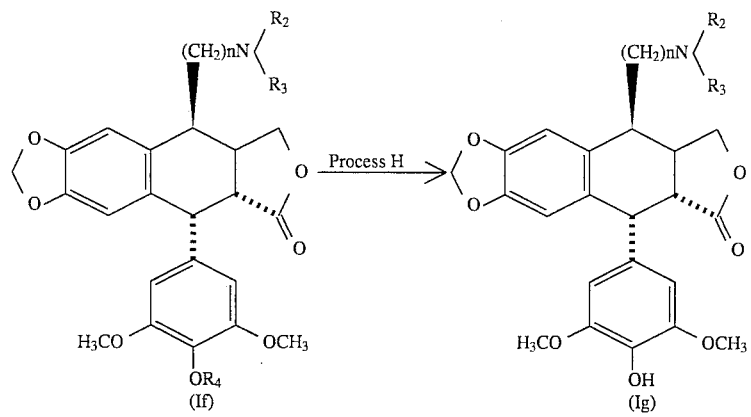

In the above formulas, $R_4$ is a methyl group, a benzyloxycarbonyl group, a lower alkanoyl group which may have one or more halogen atoms or a group of the formula —Si(Rx)(Ry)(Rz) (where Rx, Ry and Rz are as defined above); $R_5$ is a lower alkenyl group; $R_6$ is a hydroxy-containing lower alkyl group; $R_7$ is a group of the formula —$(CH_2)_m$CHO (where m is as defined above) or a lower alkyl group having a ketoaldehyde group; $R_8$ is a group of the formula —$(CH_2)_m$CHO; $R_9$ is a methyl group, a benzyloxycarbonyl group, a lower alkanoyl group which may have a halogen atom or a group of the formula —Si(Rx)(Ry)(Rz) (where Rx, Ry and Rz are as defined above); $R_2$, $R_3$ and n are respectively as defined above; provided, however, that $R_4$ and $R_9$ are not the same.

Each of the processes shown schematically above is now explained.

Process A

The known 4-epipodophyllotoxin of general formula (II) is reacted with a lower alkenylsilane of general formula (III) in the presence of a Lewis acid in an appropriate solvent to give a desired derivative of general formula (Ia) which corresponds to general formula (I) wherein R is a lower alkenyl group. The solvent is not specifically limited insofar as it does not participate in the reaction. Useful solvents include, for example, aprotic solvents such as halogenated hydrocarbons, e.g. dichloromethane, chloroform, 1,2-dichloroethane, etc. and ethers, e.g. tetrahydrofuran, dioxane, etc. The Lewis acid that may be used includes, for example, titanium tetrachloride, trimethylsilyl trifluoromethane-sulfonate, zinc bromide, boron trifluoride-ethyl ether and so on. For this reaction, the compound of general formula (III) is preferably used in a proportion of 1 to 5 mol equivalents based on the compound of general formula (II) and the Lewis acid is preferably used in a proportion of 0.5 to 3 mol equivalents based on the compound of general formula (II). The reaction temperature is –100° to 100° C. and preferably –20 ° to 20° C.

Process B

The derivative of general formula (Ia) obtained in Process A is oxidized in an inert solvent to give a desired derivative of general formula (Ib) which corresponds to general formula (I) wherein R is a hydroxy-containing lower alkyl group. As the solvent, carbon tetrachloride, acetonitrile, acetic acid, water, pyridine, etc. may be used alone or in combination. The oxidizing agent may for example be ruthenium oxide, sodium periodate or osmium tetraoxide. For this reaction, the oxidizing agent is preferably used in a proportion of 0.1 to 2 mol equivalents relative to the compound of general formula (Ia). The reaction temperature is –10° to 80° C. and preferably 0° to 20° C.

Process C

The derivative of general formula (Ia) obtained in Process A is subjected to simultaneous oxidation and reduction in an inert solvent to give a desired derivative of general formula (Ic) which corresponds to said general formula (I) wherein R is a group of the formula —$(CH_2)_m$CHO or a lower alkyl group having a ketoaldehyde group. As the solvent, carbon tetrachloride, methylene chloride, acetic acid, water, tetrahydrofuran, pyridine, etc. can be used alone or in combination. The reducing agent may for example be borane-dimethyl sulfide, thiamylborane-dimethyl sulfide or the like, while the oxidizing agent may for example be chromic acid or pyridinium chlorochromate. For this reaction, the reducing agent is preferably used in a proportion of 0.5 to 2 mol equivalents and the oxidizing agent in a proportion of 1 to 3 mol equivalents, both based on the compound of general formula (Ia). The reaction temperature is –10° to 50° C. and preferably 0° to 20° C.

Process D

The desired derivative of general formula (Ic) corresponding to general formula (I) wherein R is a group of the formula –$(CH_2)_m$CHO or a lower alkyl group having a ketoaldehyde group can also be obtained by oxidizing in an inert solvent the derivative of general formula (Ib) obtained in Process B. As the solvent, carbon tetrachloride, methylene chloride, acetic acid, tetrahydrofuran, diethyl ether, benzene, etc. can be used alone or in combination. The oxidizing agent may for example be potassium permanganate, lead tetraacetate, pyridinium chlorochromate or the like. For this reaction, the oxidizing agent is preferably used in a proportion of 0.8 to 3 mol equivalents relative to the compound of general formula (Ib). The reaction temperature is 0° to 50° C. and preferably 0° to 20° C.

Process E

The derivative of general formula (Ic) obtained in Process C or D is catalytically reduced in the presence of a catalyst in an inert solvent to give a desired derivative of general formula (Id) which corresponds to general formula (I) wherein R is a group of the formula $-(CH_2)_mCHO$. The solvent is not specifically limited insofar as it does not participate in the reaction. As the solvent, for example, ethyl acetate, methanol, tetrahydrofuran, etc. can be used alone or in combination. The catalyst may for example be palladium black, platinum or the like. The hydrogen pressure may be 1 to 3 atmospheres and preferably 1 to 2 atmospheres. The reaction temperature is 0° to 40° C. and preferably room temperature.

Process F

The derivative of general formula (Id) obtained in Process E is reacted with an acylating agent or a silylating agent in the presence of a base in an inert solvent to give a desired derivative of general formula (Ie). The solvent is not specifically limited insofar as it does not participate in the reaction and carbon tetrachloride, methylene chloride, tetrahydrofuran, benzene, dimethylformamide, dimethylacetamide, etc. can be used alone or in combination. The base may for example be pyridine, dimethylaminopyridine, imidazole or the like. The acylating agent includes acid anhydrides such as acetic anhydride, propionic anhydride, butyric anhydride, isobutyric anhydride, valeric anhydride, chloroacetic anhydride, etc. and acid halides such as acetyl chloride, propionyl chloride, n-hexanoyl chloride, chloroacetyl chloride, dichloroacetyl chloride, trichloroacetyl chloride, benzyloxycarbonyl chloride and so on. The silylating agent includes t-butyldimethylsilyl chloride, triisopropylsilyl chloride, t-butyldiphenylsilyl chloride and so on. For this reaction, the base is preferably used in a proportion of 0.01 to 7 mol equivalents and the acylating agent or the silylating agent is preferably used in a proportion of 1 to 5 mol equivalents, both based on the compound of general formula (Id). The reaction temperature is 0° to 50° C. and preferably 0° to 20° C.

Process G

The derivative of general formula (Ic) obtained in Process C or D is subjected to reductive amination with an amino compound of general formula (IV) in an inert solvent to give a desired derivative of general formula (If) which corresponds to general formula (I) wherein R is a group of the formula $-(CH_2)_nNR_2R_3$. The solvent is not specifically limited insofar as it does not participate in the reaction. Thus, for example, alcohols such as methanol, ethanol, etc., ethers such as tetrahydrofuran, dioxane, etc., organic acids such as acetic acid, formic acid, etc., water and so on can be used alone or in combination. The reducing agent may for example be sodium borohydride, sodium cyanoborohydride or the like. For this reaction, the amino compound of general formula (IV) is preferably used in a proportion of 0.9 to 3 mol equivalents and the reducing agent is preferably used in a proportion of 1 to 3 mol equivalents, both based on the compound of general formula (Ic). The reaction temperature is 0° to 50° C. and preferably 0° to 20° C.

Process H

The derivative of general formula (If) obtained in Process G is catalytically reduced in the presence of a catalyst in an inert solvent to give a desired derivative of general formula (Ig). The solvent is not particularly limited insofar as it does not participate in the reaction. Thus, for example, ethyl acetate, methanol, tetrahydrofuran, acetonitrile, etc. can be used alone or in combination. The catalyst may for example be palladium black, platinum or the like. The hydrogen pressure may be 1 to 3 atmospheres and preferably 1 to 2 atmospheres. The reaction temperature is 0° to 40° C. and preferably room temperature.

The compound of the invention as obtained by any of the above reactions can be converted to salts by the known procedures, for example by reacting it with said organic acid or inorganic acid in a solvent, such as methylene chloride, 1,2-dichloroethane, tetrahydrofuran, ethyl acetate, etc., at a temperature in the neighborhood of room temperature.

The compounds (Ia), (Ib), (Ic), (Id), (Ie), (If) and (Ig) as obtained in the above manner can be isolated and purified by the procedures used commonly in this technical field, such as concentration, filtration, recrystallization, various types of chromatography and so on.

For use as a therapeutic drug for malignant tumors in mammals including man, the compound of the present invention can be provided in a variety of pharmaceutical preparations such as oral preparations, injectable preparations, suppositories, etc., each of which can be prepared by the established pharmaceutical procedure.

In the formulation of solid preparations for oral administration, the compound of the invention is formulated with an excipient and, when required, a binder, disintegrator, lubricant, coloring agent, corrigent, flavor, etc. and processed into tablets, coated tablets, granules, powders, capsules, etc. in a usual manner. The additives are those already used in the art. For example, the excipient includes lactose, sucrose, sodium chloride, glucose, starch, calcium carbonate, kaolin, microcrystalline cellulose, silicic acid, etc. The binder includes water, ethanol, propanol, simple syrup, glucose solution, starch solution, gelatin solution, carboxymethylcellulose, hydroxypropylcellulose, hydroxypropyl-starch, methylcellulose, ethylcellulose, shellac, calcium phosphate, polyvinylpyrrolidone and so on. The disintegrator includes dried starch, sodium alginate, agar powder, sodium hydrogen carbonate, calcium carbonate, sodium lauryl sulfate, stearyl monoglyceride, lactose and so on. The lubricant includes purified talc, stearic acid salts, borax, polyethylene glycol and so on. The corrigent includes sucrose, orange peel, citric acid, tartaric acid and so on.

For the formulation of liquid preparations for oral administration, the compound of the invention can be formulated with a corrigent, buffer, stabilizer, flavor and/or the like and the resulting composition be processed into oral solutions, syrups, elixirs, etc. in a usual manner. The corrigent for this purpose may be any of those mentioned above. The buffer may for example be sodium citrate and the stabilizer may for example be tragacantha, gum arabic, gelatin or the like.

For the formulation of injectable preparations, the compound of the invention can be formulated with a pH adjusting agent, buffer, stabilizer, isotonic agent, local anesthetic, etc. and be processed into injections for subcutaneous, intramuscular or intravenous. The pH adjusting agent and buffer that can be used include sodium citrate, sodium acetate, sodium phosphate and so on. The stabilizer includes sodium pyrosulfite, EDTA, thioglycolic acid, thiolactic acid and so on. The local anesthetic includes procaine hydrochloride, lidocaine hydrochloride and so on.

For the formulation of suppositories, the compound of the invention can be formulated with a pharmaceutical carrier well known in the art, such as polyethylene glycol, lanolin, cacao butter, fatty acid triglyceride, Witepsol (trademark), etc. and, where necessary, with a surfactant such as Tween (trademark) and the resulting composition be processed into suppositories in a usual manner.

The amount of the compound of the present invention in any of the above-mentioned unit dosage forms depends on the clinical condition of the patient to be treated and the particular dosage form selected. Generally, however, the preferred amount per dosage unit is about 1 to 1000 mg for oral preparations, about 0.1 to 500 mg for injections and about 5 to 1000 mg for suppositories. The daily dosage of any pharmaceutical preparation mentioned above is also dependent on the patient's condition, body weight, age, sex and other factors but it is generally recommendable to administer about 0.1 to 5000 mg, preferably 1 to 1000 mg, per day for an adult patient, either in a single dose or in 2 to 4 divided doses.

BEST MODE FOR CARRYING OUT THE INVENTION

The following examples, pharmacological tests and preparation examples are further illustrative of the invention.

EXAMPLE 1

Synthesis of 4-desoxy-4'-demethyl-4'-O-benzyloxycarbonyl-4-allyl-4-epipodophyllotoxin (Compound 1)

To a solution of 1 g (1.87 mmol) of 4'-demethyl-4'-O-benzyloxycarbonyl-4-epipodophyllotoxin in 15 ml of dichloromethane was added 426 mg (3.73 mmol) of trimethylallylsilane and the mixture was cooled to −10° C. To this solution was added 0.6 ml of boron trifluoride ethyl ether and the mixture was stirred for 1 hour. After the reaction, 0.6 ml of pyridine was added and the mixture was poured in cold diluted hydrochloric acid and extracted with ethyl acetate. The organic layer was dried and distilled and the residue was purified by column chromatography (silica 50 g, eluent: chloroform). The eluate was concentrated and crystallized from ether to give 1 g (yield 95.7%) of 4-desoxy-4'-demethyl-4'-O-benzyloxycarbonyl-4-allyl-4-epipodophyllotoxin (Compound 1).

m.p.: 135°–137° C.

$[\alpha]^{20}_D = -70.03°$ (c=1.30, DMSO)

$^1$H-NMR ( CDCl$_3$) δppm:

7.30–7.43 (5H, m, —OCOOCH$_2$Ph), 6.72 (1H, s, 5-H), 6.46 (1H, S, 8-H), 6.31 (2H, s, 2'-H, 6'-H), 5.94 (1H, d, J=1.5 Hz, —OCH$_2$O—), 5.93 (1H, d, J=1.5 Hz, —OCH$_2$O—), 5.80 (1H, d-d-t, J=17, 10.5, 6.5 Hz, —CH$_2$CH=CH$_2$), 5.25 (2H, s, —OCOOCH$_2$Ph), 5.12 (1H, d-d-t, J=17, 2, 1.5 Hz, —CH$_2$CH=C$_2$), 5.11 (1H, d-q, J=10.5, 1.5 Hz, —CH$_2$CH=CH$_2$), 4.58 (1H, d, J=5 Hz, 1-H), 4.25 (2H, m, 11-H), 3.68 (6H, s, 3'—OCH$_3$, 5'—OH$_3$), 3.27 (1H, m, 4-H), 3.07 (1H, d-d, J=14.5, 5 Hz, 2-H), 2.93 (1H, m, 3-H), 2.57 (1H, m, —CH$_2$CH=CH$_2$), 2.42 (1H, m, —CH$_2$CH=CH$_2$)

EXAMPLE 2

Synthesis of 4-desoxy-4'-demethyl-4'-O-benzyloxycarbonyl-4-(2,3-dihydroxy-1-propyl)-4-epipodophyllotoxin (Compound 2)

To a solution of 1 g (1.79 mmol) of 4-desoxy-4'-demethyl-4'-O-benzyloxycarbonyl-4-allyl-4-epipodophyllotoxin, obtained in Example 1, in 2 ml of pyridine was added 455 mg (1.79 mmol) of osmium tetraoxide and the mixture was stirred at room temperature for 1 hour. Following this reaction, a solution of 0.8 g of sodium hydrogensulfite in aqueous pyridine was added and the mixture was further stirred for 30 minutes. The reaction mixture was extracted with ethyl acetate and the extract was washed with diluted hydrochloric acid and water and dried. The organic layer was concentrated and the residue was purified by column chromatography (silica 50 g, eluent: chloroform-methanol= 20:1). The eluate was concentrated and the residue was crystallized from ether to give 1.0 g (yield 94.2%) of 4-desoxy-4'-demethyl-4'-O-benzyloxycarbonyl-4-(2,3-dihydroxy-1-propyl)-4-epipodophyllotoxin (Compound 2).

m.p.: 170.5°–172° C.

$[\alpha]^{20}_D = -62.25°$ (c=0.66, DMSO)

$^1$H-NMR (DMSO-d$_6$) δppm:

7.40 (5H, s, —OCOOCH$_2$Ph), 6.94, 6.84 (1H, s, 5-H), 6.44 (1H, s, 8-H), 6.34, 6.32 (2H, s, 2'-H, 6'-H), 5.96 (2H, s, —OCH$_2$O—), 5.23 (2H, s, —OCOOCH$_2$Ph), 4.78 (1H, m, —CH$_2$CH(OH)CH$_2$OH), 4.58 (1H, d, J=6.0 Hz, 1-H), 4.52 (1H, m, —CH$_2$CH(OH)CH$_2$OH), 4.35 (1H, m, 11α-H) , 4.17 (1H, m, 11β-H), 3.62 (6H, s, 3'—OCH$_3$, 5'-OCH$_3$), 3.17–3.69 (4H, m, —CH$_2$CH(OH)CH$_2$OH, 4-H), 2.94–3.02 (1H, m, 2-H), 2.19 (1H, m, 3-H), 1.67 (1H, m, —CH$_2$CH(OH)CH$_2$OH), 1.24–1.32 (1H, m, —CH$_2$CH(OH)CH$_2$OH)

EXAMPLE 3

Synthesis of 4-desoxy-4'-demethyl-4'-O-benzyloxycarbonyl-4-formylmethyl-4-epipodophyllotoxin (Compound 3)

To a solution of 1 g (1.69 mmol) of 4-desoxy-4'-demethyl-4'—O-benzyloxycarbonyl-4-(2,3-dihydroxy-1-propyl)-4-epipodophyllotoxin, obtained in Example 2, in 80 ml of benzene was added 795 mg (1.79 mmol) of lead tetraacetate and the mixture was stirred at room temperature for 30 minutes. The reaction mixture was then filtered and the filtrate was concentrated. The residue was purified by column chromatography (silica 70 g, eluent: chloroform-methanol=20:1) and crystallized from ether to give 934 mg (yield 98.7%) of 4-desoxy-4'-demethyl-4'-O-benzyloxycarbonyl-4-formylmethyl-4-epipodophyllotoxin (Compound 3).

m.p.: 180°–182° C.

$[\alpha]^{20}_D = -71.04°$ (c=1.32, DMSO)

$^1$H-NMR (DMSO-d$_6$) δppm:

9.73 (1H, s, —CHO), 7.39 (5H, s, —OCOOCH$_2$Ph), 6.88 (1H, s, 5-H), 6.46 (1H, s, 8-H), 6.35 ( 2H, s, 2'-H, 6'-H), 5.96 (2H, s, —OCH$_2$O), 5.23 (2H, s, —OCOOCH$_2$ Ph ), 4.54 (1H, d, J=3.6 Hz, 1-H), 3.96–4.32 (1H, m, 11α-H), 3.63 (6H, s, 3'—OCH$_3$, 5'—OCH$_3$), 3.48–3.92 (1H, m, 11β-H), 2.56–3.40 (5H, m, 2-H, 3-H, 4-H, —CH$_2$CHO)

EXAMPLE 4

Synthesis of 4-desoxy-4'-demethyl-4'-O-benzyloxycarbonyl-4-(2-formyl-1-ethyl)-4-epipodophyllotoxin (Compound 4)

To a solution of 4 g (7.17 mmol) of 4-desoxy-4'-demethyl-4'-O-benzyloxycarbonyl-4-allyl-4-epipodophyllotoxin, obtained in Example 1, in 40 ml of tetrahydrofuran was added 4.3 ml (8.6 mmol) of a 2M solution of boran-dimethyl sulfide in tetrahydrofuran dropwise with ice-cooling and the mixture was then reacted at room temperature for 1 hour. The reaction mixture was concentrated and the residue was dissolved in 80 ml of methylene chloride followed by addition of 3.0 g (13.9 mmol) of pyridinium chlorochromate. The mixture was stirred at room temperature. After the reaction, 100 ml of ethyl acetate was added and the insoluble matter was filtered off with the aid of Florisil. The filtrate was concentrated and the residue was purified by column chromatography (silica 50 g, eluent: hexane-ethyl acetate =1:1) and crystallized from ether to give 1.85 g (yield 44.9%) of 4-desoxy-4'-demethyl-4'-O-benzyloxycarbonyl-4-(2-formyl-1-ethyl)-4-epipodophyllotoxin (Compound 4).

m.p.: 153°–155° C.

$[\alpha]^{20}_D = -69.09°$ (c=0.38, DMSO)

$^1$H-NMR (CDCl$_3$) δppm:

9.83 (1H, s, —CHO), 7.40 (5H, m, —OCOOCH$_2$Ph), 6.83 (1H, s, 5-H), 6.45 (1H, s, 8-H), 6.28 (2H, s, 2'-H, 6'-H), 5.94 (2H, s, —OCH$_2$O), 5.25 (2H, s, —OCOOCH$_2$Ph), 4.58 (1H, d, J=4.6 Hz, 1-H), 4.37 (1H, m, 11α-H), 4.11 (1H, m, 11β-H), 3.67 (6H, s, 3'—OCH$_3$, 5'—OCH$_3$), 3.04–3.10 (1H, m, 4-H), 2.86–3.00 (2H, m, 2-H, 3-H), 2.49–2.67 (2H, m, —CH$_2$CHO), 1.83–2.21 (2H, m, —CH$_2$CH$_2$CHO)

EXAMPLE 5

Synthesis of 4-desoxy-4'-demethyl-4-formylmethyl-4-epipodophyllotoxin (Compound 5)

To a solution of 100 mg (0,178 mmol) of 4-desoxy-4'-demethyl-4'-O-benzyloxycarbonyl-4-formylmethyl-4-epipodophyllotoxin, obtained in Example 3, in 10 ml of ethyl acetate-methanol (1:1) was added 30 mg of 5% palladium-on-carbon, and catalytic reduction was carried out in hydrogen streams (at atmospheric pressure). Following this reaction, the 5% palladium-on-carbon was filtered off and the filtrate was concentrated under reduced pressure. The residue was crystallized from ether to give 75 mg (yield 98.9%) of 4-desoxy-4'-demethyl-4-formylmethyl-4-epipodophyllotoxin (Compound 5).

m.p.: 237°–239° C.

$[\alpha]^{20}_D = -110.12°$ (c=0.38, DMSO)

$^1$H-NMR (CDCl$_3$) δppm:

9.72 (1H, s, —CHO), 8.22 (1H, s, 4'—OH), 6.86 (1H, s, 5-H), 6.43 (1H, s, 8-H), 6.21 (2H, s, 2'-H, 6'-H), 5.96, 5.94 (2H, s, —OCH$_2$O), 4.41 (1H, d, J=5.28 Hz, 1-H), 4.15 (1H, d-d, J=7.9, 3.9 Hz, 11α-H), 3.66–3.73 (1H, m, 11β-H), 3.62 (6H, s, 3'—OCH$_3$, 5'—OCH$_3$), 2.56–3.40 (5H, m, 2-H, 3-H, 4-H, —C$_2$CHO)

EXAMPLE 6

Synthesis of 4-desoxy-4'-demethyl-4'-O-benzyloxycarbonyl-4-(2-oxo-2-formyl-1-ethyl)-4-epipodophyllotoxin (Compound 6)

To a solution of 100 mg (0.17 mmol) of 4-desoxy-4'-demethyl-4'-O-benzyloxycarbonyl-4-(2,3-dihydroxy-1-propyl)-4-epipodophyllotoxin, prepared in Example 2, in 5 ml of methylene chloride was added 73 mg (0.34 mmol) of pyridinium chlorochromate and the mixture was stirred at room temperature for 1 hour. After the reaction, ethyl acetate was added and the organic layer was washed with cold diluted hydrochloric acid and saturated aqueous sodium chloride solution and dried over magnesium sulfate. The solvent was distilled off and the residue was purified by column chromatography (silica 20 g, eluent: chloroform-methanol=20:1) and crystallized from ether to give 45 mg (yield 45.0%) of 4-desoxy-4'-demethyl-4'-O-benzyloxycarbonyl-4-(2-oxo-2-formyl-1-ethyl)-4-epipodophyllotoxin (Compound 6).

$^1$H-NMR (CDCl$_3$) δppm:

9.85 (1H, s, —CH$_2$COCHO), 7.38 (5H, m, —OCOOCH$_2$Ph), 6.61 (1H, s, 5-H), 6.45 (1H, s, 8-H), 6.31 (2H, s, 2'-H, 6'-H), 5.93 (2H, s, —OCH$_2$O—), 5.25 (2H, s, —OCOOCH$_2$Ph), 4.55 (1H, d, J=3.6 Hz, 1-H), 4.12–4.40 (1H, m, 11α-H), 3.48–4.00 (1H, m, 11β-H), 3.68 (6H, s, 3'—OCH$_3$, 5'-OCH$_3$), 2.60–3.08 (5H, m, 2-H, 3-H, 4-H, —CH$_2$COCHO)

EXAMPLE 7

Synthesis of 4-desoxy-4'-demethyl-4'-O-chloroacetyl-4-formylmethyl-4-epipodophyllotoxin (Compound 7)

To a solution of 50 mg (0.117 mmol) of 4-desoxy-4'-demethyl-4-formylmethyl-4-epipodophyllotoxin, obtained in Example 5, in 5 ml of tetrahydrofuran were added 50 mg (0.292 mmol) of chloroacetic anhydride and 10 mg (0.081 mmol) of dimethylaminopyridine and the mixture was stirred at room temperature overnight. After the reaction, the solvent was distilled off and the residue was purified by preparative thin-layer chromatography (eluent: chloroform-methanol=30:1). The residue obtained by extraction was crystallized from ethyl acetate-n-hexane and the crystals were collected by filtration to give 50 mg (yield 90.0%) of 4-desoxy-4'-demethyl-4'-O-chloroacetyl-4-formylmethyl-4-epipodophyllotoxin (Compound 7).

m.p.: 119°–121° C, $[\alpha]^{20}_D = -85.21°$ (c=0.399, DMSO)

$^1$H-NMR (CDCl$_3$) δppm:

9.64 (1H, s, —CHO), 6.40 (1H, s, 5-H), 6.25 (1H, s, 8-H), 6.10 (2H, s, 2'-H, 6'-H), 5.73 (1H, S, —OCH$_2$O—), 5.7 2 (1H, d, J=4.9 Hz, 1-H), 4.12 (2H, s, ClCH$_2$CO—) 4.06 (1H, d, J=7.2 HZ, 11α-H), 3.61 (1H, m, 11β-H), 3.46 (6H, s, 3'—OCH$_3$, 5'—OCH$_3$), 3.37 (1H, t, J=10.5 Hz, 2-H), 2.51–2.85 (4H, m, 3-H, 4-H, —CH$_2$CHO)

EXAMPLE 8

Synthesis of 4-desoxy-4'-demethyl-4'-O-trichloroacetyl-4-formylmethyl-4-epipodophyllotoxin (Compound 8)

To a solution of 4.26 g (10 mmol) of 4-desoxy-4'-demethyl-4-formylmethyl-4-epipodophyllotoxin, obtained in Example 5, in 50 ml of methylene chloride were added 2.36 g (13 mmol) of trichloroacetyl chloride and 1.58 g (13 mmol) of dimethylaminopyridine and the mixture was stirred at room temperature overnight. After the reaction, the solvent was distilled off and the residue was purified by column chromatography (eluent: ethyl acetate-n-hexane=1:1). The eluate was crystallized from methanol and the crystals were collected by filtration to give 4.10 g (yield 71.7%) of 4-desoxy-4'-demethyl-4'-O-trichloroacetyl-4-formylmethyl-4epipodophyllotoxin (Compound 8).

m.p.: 177°–178° C.

$[\alpha]^{20}_D = -68.96°$ (c=0.58, DMSO)

$^1$H-NMR (CDCl$_3$) δppm:

9.88 (1H, s, —CHO), 6.63 (1H, s, 5-H), 6.47 (1H, s, 8-H), 6.35 (2H, s, 2'-H, 6'-H), 5.96 (1H, s, —OCH$_2$O), 4.61 (1H, d, J=5.2 Hz, 1-H), 4.30 (1H, t, J=8.9 Hz, 11α-H), 3.80 (1H, m, 11β-H), 3.72 (6H, s, 3'—OCH$_3$,

5'—OCH3), 3.60 (1H, t, J=9.6 Hz, 2-H), 2.70–3.10 (4H, m, 3-H, 4-H, —CH$_2$CHO)

EXAMPLE 9

Synthesis of 4-desoxy-4'-demethyl-4'-O-acetyl-4-formylmethyl-4-epipodophyllotoxin (Compound 9)

To a solution of 50 mg (0.117 mmol) of 4-desoxy-4'-demethyl-4-formylmethyl-4-epipodophyllotoxin, obtained in Example 5, in 5 ml of tetrahydrofuran were added 50 mg (0.49 mmol) of acetic anhydride and 10 mg (0.081 mmol) of dimethylaminopyridine and the mixture was stirred at room temperature overnight. After the reaction, the solvent was distilled off and the residue was purified by preparative thin-layer chromatography (eluent: chloroform-methanol= 30:1). The residue obtained by extraction was crystallized from n-hexane and the crystals were collected by filtration to give 40 mg (yield 73.0%) of 4-desoxy-4'-demethyl-440-O-acetyl-4-formylmethyl-4-epipodophyllotoxin (Compound 9).

m.p.: 130°–133° C.

$[\alpha]^{20}{}_D = -88.40°$ (c=0.5, DMSO)

$^1$H-NMR (CDCl$_3$) δppm:

9.55 (1H, s, —CHO), 6.30 (1H, s, 5-H), 6.16 (1H, s, 8-H), 5.99 (2H, s, 2'-H, 6'-H), 5.63 (1H, s, —OCH$_2$O), 5.62 (1H, s, —OCH$_2$O), 4.27 (1H, d, J=4.9 Hz, 1-H), 3.98 (1H, t, J=8.2 Hz, 11α-H), 3.51 (1H, m, 11β-H), 3.37 (6H, s, '—OCH$_3$, 5'—OCH$_3$), 3.28 (1H, t, J=9.9 Hz, 2-H), 2.42–2.75 (4H, m, 3-H, 4-H, —CH$_2$CHO), 1.97 (3H, s, —OCOCH$_3$)

EXAMPLE 10

Synthesis of 4-desoxy-4'-demethyl-4'-O-t-butyldiphenylsilyl-4-formylmethyl-4-epipodophyllotoxin (Compound 10)

To a solution of 50 mg (0.117 mmol) of 4-desoxy-4'-demethyl-4-formylmethyl-4-epipodophyllotoxin, obtained in Example 5, in 5 ml of dimethylformamide were added 33 mg (0.12 mmol) of t-butyldiphenylsilyl chloride and 79 mg (0.64 mmol) of dimethylaminopyridine and the mixture was stirred at room temperature overnight. The reaction mixture was then extracted with ethyl acetate-water and dried. The solvent was then distilled off and the residue was purified by preparative thin-layer chromatography (eluent: chloroform-methanol=30:1). The residue obtained by extraction was dried under reduced pressure to give 35 mg (yield 37.4%) of 4-desoxy-4'-demethyl-4'-O-t-butyldiphenylsilyl-4-formylmethyl-4-epipodophyllotoxin (Compound 10).

$^1$H-NMR (CDCl$_3$) δppm:
9.71 (1H, s, —CHO), 7.71 (4H, m,

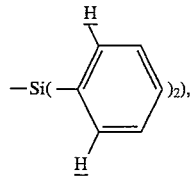

7.38 (6H, m,

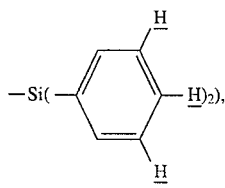

6.50 (1H, s, 5-H), 6.38 (1H, s, 8-H), 6.06 (2H, s, 2'-H, 6'-H), 5.87 (2H, s, —OCH$_2$O), 4.40 (1H, d, J=4.9 Hz, 1-H), 4.16 (1H, t, J=7.5 Hz, 11α-H), 3.70 (1H, m, 11β-H), 3.43 (1H, t, J=9.5 Hz, 2-H), 3.28 (6H, s, 3'—OCH$_3$, 5'—OCH$_3$), 2.47–2.84 (4H, m, 3-H, 4-H, —CH$_2$CHO), 1.05 (9H, s, -Si-t-Bu)

EXAMPLE 11

Synthesis of 4-desoxy-4-formylmethyl-4-epipodophyllotoxin (Compound 11)

To a solution of 500 mg (1.2 mmol) of 4-epipodophyllotoxin in 10 ml of dichloromethane was added 274 mg (2.4 mmol) of trimethylallylsilane and the mixture was cooled to −10°–0° C. To this solution was added 0.35 ml of boron trifluoride ethyl ether and the mixture was stirred for 4 hours. After 0.35 ml of pyridine was added, the reaction mixture was extracted with ethyl acetate. The organic layer was dried and distilled and the residue was purified by column chromatography (silica 50 g, eluent: ethyl acetate-hexane=1:2). The eluate was crystallized from ether-hexane and the crystals were collected by filtration to give 450 mg (yield 81.1%) of 4-desoxy-4-allyl-4-epipodophyllotoxin. Then, to a solution of 200 mg (0.46 mmol) of this compound in pyridine (4 ml) was added 116 mg (0.46 mmol) of osmium tetraoxide and the mixture was stirred at room temperature for 1 hour. After the reaction, a solution of 0.1 g of sodium hydrogensulfite in aqueous pyridine was added and the mixture was stirred for 30 minutes. This reaction mixture was extracted with ethyl acetate and the extract was washed with diluted hydrochloric acid and water and dried. The organic layer was concentrated and the residue was purified by column chromatography (silica 50 g, eluent: chloroform-methanol=20:1). The eluate was concentrated and, then, crystallized from ether-hexane to give 194 mg (yield 89.3%) of 4-desoxy-4-(2,3-dihydroxy-1-propyl)-4-epipodophyllotoxin.

m.p.: 144°–145° C.

$[\alpha]^{20}{}_D = -73.42°$ (c=0 52 CHCl$_3$)

Then, to a solution of 100 mg (0.21 mmol) of this compound in 10 ml of benzene was added 113 mg (0.25 mmol) of lead tetraacetate and the mixture was stirred at room temperature for 20 minutes. The reaction mixture was then filtered and the filtrate was concentrated. The residue was purified by column chromatography (silica 20 g, eluent: chloroform-methanol=20:1) and crystallized from ether-hexane (1:1) to give 90 mg (yield 97.4%) of 4-desoxy-4-formylmethyl-4-epipodophyllotoxin (Compound 11).

m.p.: 157°–159° C.

$[\alpha]^{20}{}_D = -105.82°$ (c=1.253, DMSO)

$^1$H-NMR (CDCl$_3$) δppm:

9.84 (1H, s, —CHO), 6.29 (1H, s, 5-H), 6.46 (1H, s, 8-H), 6.28 (2H, s, 2'-H, 6'-H), 5.93 (2H, s, —OCH$_2$O), 4.52 (1H, d, J=3.6 Hz, 1-H), 4.12–4.36 (1H, m, 11α-H), 3.79 (3H, s, 4'—OCH$_3$), 3.74 (6H, s, 3'—OCH$_3$, 5'-OCH$_3$), 3.40–3.92 (1H, m, 11β-H), 2.56–3.24 (5H, m, 2-H, 3-H, 4-H, —CH$_2$CHO)

EXAMPLE 12

Synthesis of 4-desoxy-4'-demethyl-4'-O-benzyloxycarbonyl-4-(3-N,N-dimethylamino-1-propyl)-4epipodophyllotoxin (Compound 12)

To a mixture of 0.1 ml of 50% aqueous solution of dimethylamine and 3 ml of methanol were added 0.1 ml of acetic acid and 35 mg (0.56 mmol) of sodium cyanoborohydride, followed by addition of 300 mg (0.52 mmol) of 4-desoxy-4'-demethyl-4'-O-benzyloxycarbonyl-4-(2-formyl-1-ethyl)-4-epipodophyllotoxin obtained in Example 4. The mixture was reacted at room temperature for 1 hour. Then, after 30 ml of chloroform was added, the reaction mixture was washed with saturated aqueous sodium hydrogen carbonate solution and water and dried over magnesium sulfate. The solvent was then distilled off and the residue was purified by column chromatography (silica 20 g, eluent: chloroform-methanol=20:1) to give 245 mg (yield 78%) of 4-desoxy-4'-demethyl-4'-O-benzyloxycarbonyl-4-(3-N,N-dimethylamino-1-propyl)-4-epipodophyllotoxin (Compound 12).

EXAMPLE 13

Synthesis of 4-desoxy-4'-demethyl-4'-O-benzyloxycarbonyl-4-(3-N,N-dimethylamino-1-ethyl)-4epipodophyllotoxin (Compound 13)

To a mixture of 15 mg (0.167 mmol) of 50% aqueous solution of dimethylamine and 5 ml of methanol were added 0.1 ml of acetic acid and 10 mg (0.19 mmol) of sodium cyanoborohydride, followed by addition of 100 mg (0.178 mmol) of 4-desoxy-4'-demethyl-4'-O-benzyloxy-carbonyl-4-formylmethyl-4-epipodophyllotoxin obtained in Example 3, and the mixture was reacted at room temperature for 1 hour. Then, after 100 ml of ethyl acetate was added, the reaction mixture was washed with saturated aqueous sodium hydrogen carbonate solution and water and dried over magnesium sulfate. The solvent was then distilled off and the residue was purified by thin-layer chromatography (eluent: chloroform-methanol=5:1) to give 60 mg (yield 57.2%) of 4-desoxy-4'-demethyl-4'-O-benzyloxycarbonyl-4-(3-N,N-dimethylamino-1-ethyl)-4-epipodophyllotoxin (Compound 13).

EXAMPLE 14

Synthesis of 4-desoxy-4'-demethyl-4'-O-benzyloxycarbonyl-4-(2-N-methyl-N-cyclohexylamino-1-ethyl)-4-epipodophyllotoxin (Compound 14)

To a solution of 180 mg (1.81 mmol) of cyclohexylamine in 10 ml of methanol were added 0.1 ml of acetic acid and 85 mg (1.35 mmol) of sodium cyanoborohydride followed by addition of 500 mg (0.9 mmol) of 4-desoxy-4'-demethyl-4'-O-benzyloxycarbonyl-4-formylmethyl-4-epipodophyllotoxin obtained in Example 3, and the mixture was reacted at room temperature for 1 hour. To this reaction mixture was added 0.1 ml of 37% formalin and the reaction was further allowed to proceed at room temperature for 1 hour. The reaction mixture was diluted with chloroform, washed with saturated aqueous sodium hydrogen carbonate solution and water and dried over magnesium sulfate. The solvent was then distilled off and the residue was purified by column chromatography (silica 20 g, eluent: chloroform-methanol= 20:1) to give 470 mg (yield 79%) of 4-desoxy-4'-demethyl-4'-O-benzyloxycarbonyl-4-(2-N-methyl-N-cyclohexylamino-1-ethyl)-4-epipodophyllotoxin (Compound 14).

EXAMPLE 15

Synthesis of 4-desoxy-4'-demethyl-4'-O-benzyloxycarbonyl-4-(2-N,N-diethylamino-1-ethyl)-4877-epipodophyllotoxin (Compound 15)

To a mixture of 38 mg (0–53 mmol) of diethylamine and 10 ml of methanol were added 0.1 ml of acetic acid and 52 mg (0.82 mmol) of sodium cyanoborohydride followed by addition of 300 mg (0.53 mmol) of 4-desoxy-4'-demethyl-4'-O-benzyloxycarbonyl-4-formylmethyl-4-epipodophyllotoxin obtained in Example 3, and the mixture was reacted at room temperature for 1 hour. This reaction mixture was diluted with chloroform, washed with saturated aqueous sodium hydrogen carbonate solution and water and dried over magnesium sulfate. The solvent was then distilled off and the residue was purified by column chromatography (silica 20 g, eluent: chloroform-methanol=20:1) to give 175 mg (yield 53.5%) of 4-desoxy-4'-demethyl-4'-O-benzyloxycarbonyl-4-(2-N,N-diethylamino-1-ethyl)-4-epipodophyllotoxin (Compound 15).

EXAMPLE 16 THROUGH 27

Compounds 16 through 27, shown in Table 1, were synthesized in the same manner as Examples 12 through 15.

TABLE 1

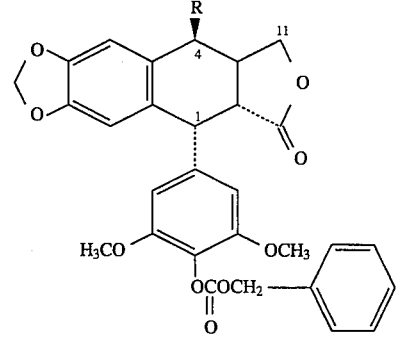

---

Compound: 12
R = —$CH_2CH_2CH_2N(CH_3)_2$
Yield: 78.0%
$^1$H-NMR [Solvent: CDCl$_3$]: δ(ppm)
7.37(5H, m, Ph$CH_2$OCO—), 6.71(1H, s, 5-H),
6.44(1H, s, 8-H), 6.30(2H, s, 2'-H, 6'-H), 5.93
(2H, s, —O$CH_2$O—), 5.25(2H, s, PhC$H_2$OCO—), 4.00–4.60
(3H, m, 1-H, 11-H), 3.67(6H, s, 3'-OC$H_3$, 5'-OC$H_3$),
3.00(3H, m, 2-H, 3-H, 4-H), 2.20–2.40(2H, m, —C$H_2$N<),
2.22(6H, s, —N(C$H_3$)$_2$), 1.66(4H, m, —C$H_2$C$H_2$C$H_2$N<)

---

Compound: 13
R = —$CH_2CH_2N(CH_3)_2$
Yield: 57.2%
$^1$H-NMR [Solvent: CDCl$_3$]: δ(ppm)
7.37(5H, m, Ph$CH_2$OCO—), 6.74(1H, s, 5-H),
6.44(1H, s, 8-H), 6.29(2H, s, 2'-H, 6'-H), 5.93
(2H, s, —O$CH_2$O—), 5.25(2H, s, PhC$H_2$OCO—),
4.56(1H, d, J=5.5Hz, 1-H), 4.00–4.28(2H, m,
11-H), 3.67(6H, s, 3'-OC$H_3$, 5'-OC$H_3$), 2.68–3.28
(3H, m, 2-H, 3-H, 4-H), 2.32(2H, t, J=7.2Hz, —C$H_2$N<)
2.27(6H, s, —N(C$H_3$)$_2$), 1.48–2.04(2H, m, —C$H_2$C$H_2$N<)

---

Compound: 14

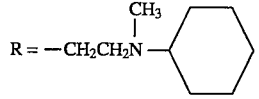

TABLE 1-continued

[Structure: tetracyclic core with methylenedioxy group, R substituent at position 4, lactone ring at position 11, and 3,5-dimethoxy-4-(benzyloxycarbonylmethoxy)phenyl group at position 1]

Yield: 79.0%
¹H-NMR [Solvent: CDCl₃]: δ(ppm)
7.46(5H, m, P̲hCH₂OCO—), 6.73(1H, s, 5-H),
6.44(1H, s, 8-H), 6.31(2H, s, 2'-H, 6'-H), 5.93
(2H, s, —OCH₂O—), 5.25(2H, s, PhCH̲₂OCO—),
4.10–4.60(3H, m, 1-H, 11-H), 3.68(6H, s, 3'-OCH̲₃,
5'-OCH̲₃), 2.80–3.16(3H, m, 2-H, 3-H, 4-H), 2.38–2.53

(3H, m, —CH̲₂N<, ⌬-H ), 2.26(3H, s, >NCH̲₃), 1.79(7H, m, —CH̲₂CH̲₂N<, ⌬-H(e) ), 1.13–1.28(5H, m,

⌬-H(aq) )

Compound: 15
R = —CH₂CH₂N(C₂H₅)₂
Yield: 53.5%
¹H-NMR [Solvent: CDCl₃]: δ(ppm)
7.45(5H, m, P̲hCH₂OCO—), 6.65(1H, s, 5-H),
6.38(1H, s, 8-H), 6.28(2H, s, 2'-H, 6'-H), 5.86
(1H, d, J=1.5Hz, —OCH₂O—), 5.85(1H, d, J=1.5Hz,
—OCH̲₂O—), 5.26(2H, s, PhCH̲₂OCO—), 4.47(1H, d, J=5.0Hz,
1-H), 4.26(1H, dd, J=9.7Hz, 11α-H), 4.06(1H, t, J=9Hz, 11β-
H), 3.71(6H, s, 3'-OCH̲₃, 5'-OCH̲₃), 3.06(1H, dt, J=7Hz,
5Hz, 4-H), 2.91(1H, dd, J=14Hz, 5Hz, 2-H), 2.87(1H,
dddd, J=14Hz, 9Hz, 7Hz, 5Hz, 3-H), 2.49(4H, q, J=7Hz,
—N(CH̲₂CH₃)₂), 2.41(2H, m, —CH₂CH̲₂N<), 1.82(1H, m,
—CH̲₂CH₂N<), 1.63(1H, m, —CH̲₂CH₂N<), 0.98(6H, t, J=7Hz,
—N(CH₂CH̲₃)₂)

Compound: 16

R = —CH₂CH₂NCH₂CH₂OH
        |
        CH₃

Yield: 79.5%
¹H-NMR [Solvent: CDCl₃]: δ(ppm)
7.37(5H, m, P̲hCH₂OCO—), 6.72(1H, s, 5-H),
6.44(1H, s, 8-H), 6.30(2H, s, 2'-H, 6'-H), 5.93
(2H, s, —OCH̲₂O—), 5.25(2H, s, PhCH̲₂OCO—),
4.00–4.60(3H, m, 1-H, 11-H), 3.67(6H, s, 3'-OCH̲₃,
5'-OCH̲₃), 2.80–3.20(5H, m, 2-H, 3-H, 4-H, —CH̲₂OH), 2.40–2.70
(4H, m, —CH̲₂NCH̲₂—), 2.30(3H, s, >NCH̲₃), 1.60–2.10
(2H, m, —CH̲₂CH₂N<)

Compound: 17

R = —CH₂CH₂N—N(CH₃)₂
        |
        CH₃

Yield: 79.9%

¹H-NMR [Solvent: CDCl₃]: δ(ppm)
7.37(5H, m, P̲hCH₂OCO—), 6.79(1H, s, 5-H), 6.43(1H,
s, 8-H), 6.31(2H, s, 2'-H, 6'-H), 5.92(2H, s, —OCH₂O—),
5.25(2H, s, PhCH̲₂OCO—), 4.54(1H, d, J=5.5Hz, 1-H),
4.10–4.40(2H, m, 11-H), 3.67(6H, s, 3'-OCH̲₃, 5'-OCH̲₃),
2.80–3.30(3H, m, 2-H, 3-H, 4-H), 2.46(2H, t, J=7.2Hz,
—CH̲₂N<), 2.33(6H, s, —N(CH₃)₂), 2.26(3H, s,
—N(CH̲₃)—N(CH₃)₂), 1.60–2.10(2H, m, —CH̲₂CH₂N<)

Compound: 18

R = —CH₂CH₂N⌬N—CH₃

Yield: 76.9%
¹H-NMR [Solvent: CDCl₃]: δ(ppm)
7.37(5H, m, P̲hCH₂OCO—), 6.74(1H, s, 5-H), 6.44(1H,
s, 8-H), 6.29(2H, s, 2'-H, 6'-H), 5.92(2H, s, —OCH₂O—),
5.24(2H, s, PhCH̲₂OCO—), 4.56(1H, d, J=5.4Hz, 1-H),
3.96–4.44(2H, m, 11-H), 3.67(6H, s, 3'-OCH̲₃, 5'-OCH̲₃), 2.76–3.28(3H, m, 2-H, 3-H, 4-H), 2.49(8H, m, —N⌬N—), 2.30(3H, s, >NCH̲₃), 2.36(2H, m, —CH̲₂N⌬N—), 2.08(2H, m, —CH̲₂CH₂N⌬N—)

Compound: 19

R = —CH₂CH₂NCH₂CH₂N(CH₃)₂
        |
        CH₃

Yield: 42.4%
¹H-NMR [Solvent: CDCl₃]: δ(ppm)
7.38(5H, m, P̲hCH₂OCO—), 6.75(1H, s, 5-H), 6.44(1H,
s, 8-H), 6.30(2H, s, 2'-H, 6'-H), 5.93(2H, s, —OCH₂O—),
5.25(2H, s, PhCH̲₂OCO—), 4.56(1H, d, J=4.5Hz, 1-H),
3.96–4.40(2H, m, 11-H), 3.67(6H, s, 3'-OCH̲₃, 5'-OCH̲₃),
2.80–3.24(3H, m, 2-H, 3-H, 4-H), 2.38–2.60(6H, m,
—CH̲₂NCH̲₂CH̲₂N<), 2.27(9H, s, —N(CH̲₃)CH₂CH₂N(CH̲₃)₂,
1.60–2.08(2H, m, —CH̲₂CH₂N(CH₃)CH₂CH₂N<)

Compound: 20

R = —CH₂CH₂NCH(CH₂OH)₂
        |
        CH₃

TABLE 1-continued

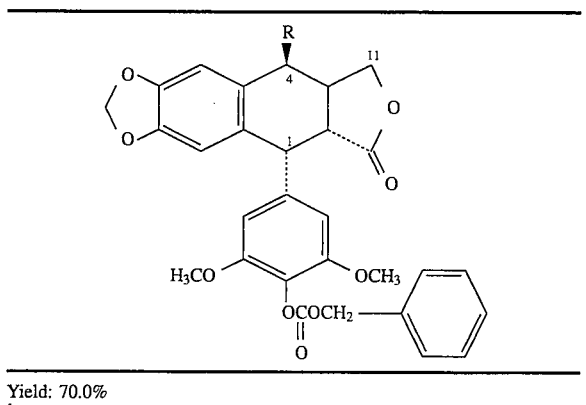

Yield: 70.0%
¹H-NMR [Solvent: CDCl₃]: δ(ppm)
7.37(5H, m, PhCH₂OCO—), 6.68(1H, s, 5-H), 6.44(1H, s, 8-H), 6.30(2H, s, 2'-H, 6'-H), 5.93(2H, s, —OCH₂O—), 5.25(2H, s, PhCH₂OCO—), 4.59(1H, d, J=3.6Hz, 1-H), 3.92–4.48(2H, m, 11-H), 3.68(6H, s, 3'-OCH₃, 5'-OCH₃), 3.66(4H, d, J=7.0Hz, —CH(CH₂OH)₂), 2.60–3.24(7H, m, 2-H, 3-H, 4-H, —CH₂NCH<), 2.37(3H, s, >NCH₃), 1.48–2.20 (4H, b, —CH₂CH₂NCH(CH₂OH)₂)

Compound: 21

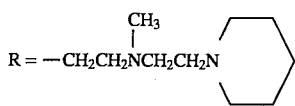
R = —CH₂CH₂NCH₂CH₂N⟨cyclohexyl⟩
      |
      CH₃

Yield: 64.0%
¹H-NMR [Solvent: CDCl₃]: δ(ppm)
7.37(5H, m, PhCH₂OCO—), 6.74(1H, s, 5-H), 6.44(1H, s, 8-H), 6.30(2H, s, 2'-H, 6'-H), 5.93(2H, s, —OCH₂O—), 5.25(2H, s, PhCH₂OCO—), 4.00–4.60(3H, m, 1-H, 11-H), 3.55(6H, s, 3'-OCH₃, 5'-OCH₃), 2.90–3.20

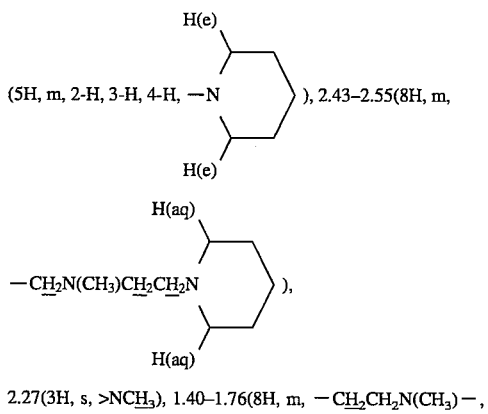

(5H, m, 2-H, 3-H, 4-H, —N), 2.43–2.55(8H, m,

—CH₂N(CH₃)CH₂CH₂N ), 2.27(3H, s, >NCH₃), 1.40–1.76(8H, m, —CH₂CH₂N(CH₃)—,

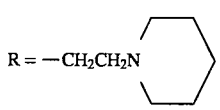
—N )

Compound: 22

R = —CH₂CH₂N⟨piperidinyl⟩

Yield: 96.0%
¹H-NMR [Solvent: CDCl₃]: δ(ppm)
7.38(5H, m, PhCH₂OCO—), 6.75(1H, s, 5-H), 6.44(1H, TABLE 1-continued

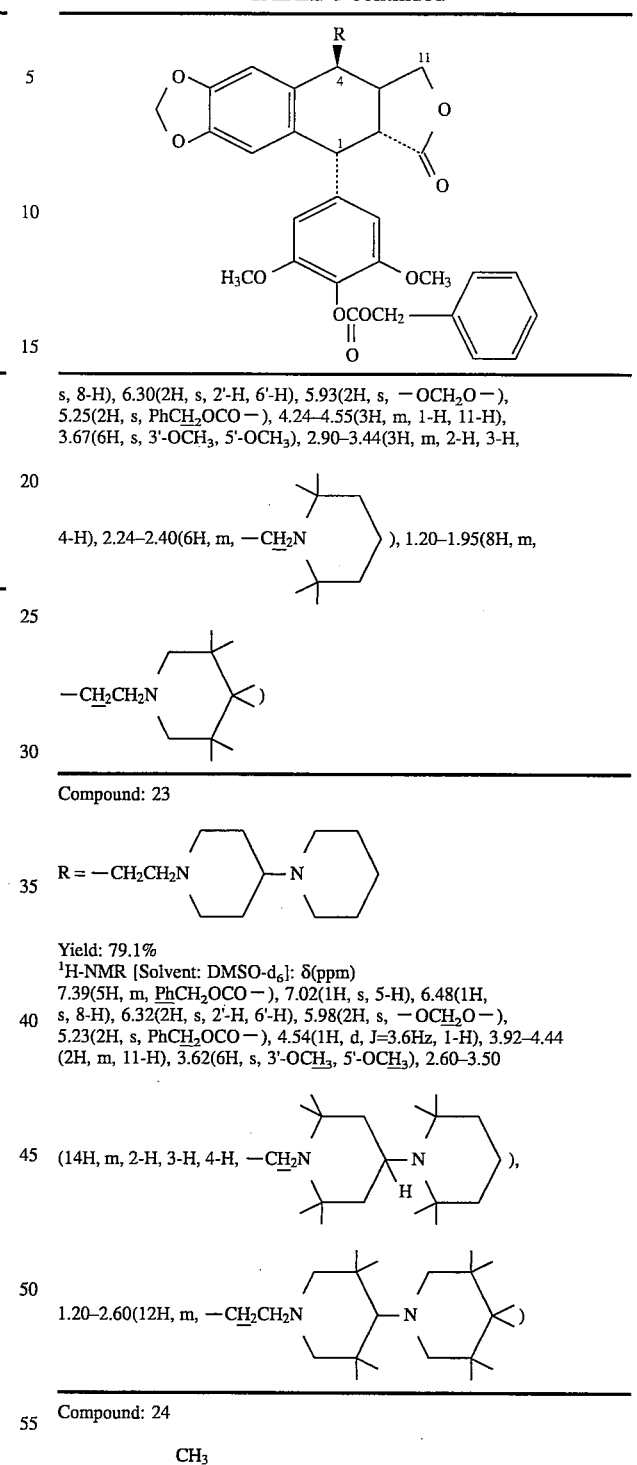

s, 8-H), 6.30(2H, s, 2'-H, 6'-H), 5.93(2H, s, —OCH₂O—), 5.25(2H, s, PhCH₂OCO—), 4.24–4.55(3H, m, 1-H, 11-H), 3.67(6H, s, 3'-OCH₃, 5'-OCH₃), 2.90–3.44(3H, m, 2-H, 3-H,

4-H), 2.24–2.40(6H, m, —CH₂N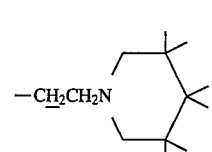), 1.20–1.95(8H, m,

—CH₂CH₂N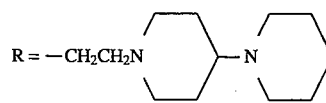)

Compound: 23

R = —CH₂CH₂N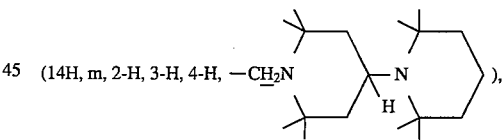

Yield: 79.1%
¹H-NMR [Solvent: DMSO-d₆]: δ(ppm)
7.39(5H, m, PhCH₂OCO—), 7.02(1H, s, 5-H), 6.48(1H, s, 8-H), 6.32(2H, s, 2'-H, 6'-H), 5.98(2H, s, —OCH₂O—), 5.23(2H, s, PhCH₂OCO—), 4.54(1H, d, J=3.6Hz, 1-H), 3.92–4.44 (2H, m, 11-H), 3.62(6H, s, 3'-OCH₃, 5'-OCH₃), 2.60–3.50

(14H, m, 2-H, 3-H, 4-H, —CH₂N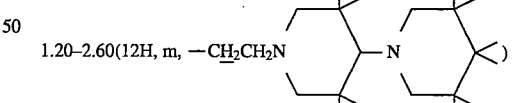), 1.20–2.60(12H, m, —CH₂CH₂N)

Compound: 24

CH₃
          |
R = —CH₂CH₂NCH₂CH₂OCH₃

Yield: 76.0%
¹H-NMR [Solvent: CDCl₃]: δ(ppm)
7.38(5H, m, PhCH₂OCO—), 6.80(1H, s, 5-H), 6.44(1H, s, 8-H), 6.30(2H, s, 2'-H, 6'-H), 5.93(2H, s, —OCH₂O—), 5.26(2H, s, PhCH₂OCO—), 4.57(1H, d, J=5.0Hz, 1-H), 4.34 (1H, t, J=9.6Hz, 11α-H), 4.14(1H, t, J=9.5Hz, 11β-H), 3.68(6H, s, 3'-OCH₃, 5'-OCH₃), 3.53(2H, t, J=5.0Hz, —CH₂OCH₃), 3.39(1H, m, 4-H), 3.37(3H, s, —CH₂OCH₃),

TABLE 1-continued

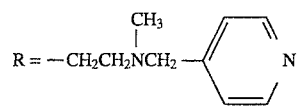

2.95–3.19(2H, m, 2-H, 3-H), 2.64(2H, m, —CH$_2$N<), 2.48 (2H, m, >NC$\underline{H}_2$CH$_2$OCH$_3$), 2.34(3H, s, >NC$\underline{H}_3$), 1.96(1H, m, —CH$_2$C$\underline{H}_2$N<), 1.72(1H, m, —C$\underline{H}_2$CH$_2$N<)

Compound: 25

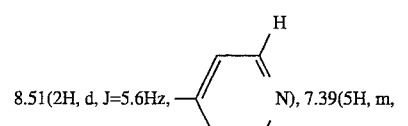

Yield: 65.0%
$^1$H-NMR [Solvent: DMSO-d$_6$]: δ(ppm)

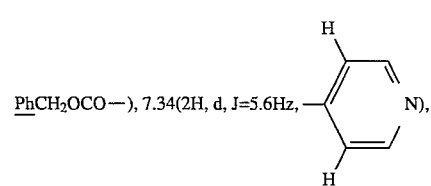

6.82(1H, s, 5-H), 6.45(1H, s, 8-H), 6.32(2H, s, 2'-H, 6'-H), 5.96(2H, s, —OC$\underline{H}_2$O—), 5.23(2H, s, PhC$\underline{H}_2$OCO—), 4.52(1H, d, J=5.9Hz, 1-H), 4.26(1H, m, 11α-H), 4.05 (1H, m, 11β-H), 3.10–3.70(4H, m, 2-H, 4-H,

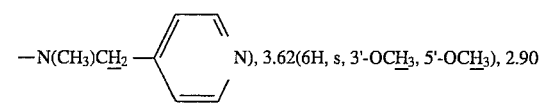

(1H, m, 3-H), 2.30–2.50(2H, m, —CH$_2$C$\underline{H}_2$N<), 2.16(3H, s, >NC$\underline{H}_3$), 2.10(1H, m, —C$\underline{H}_2$CH$_2$N<), 1.60(1H, m, —C$\underline{H}_2$CH$_2$N<)

Compound: 26

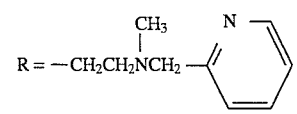

Yield: 66.0%
$^1$H-NMR [Solvent: CDCl$_3$]: δ(ppm)

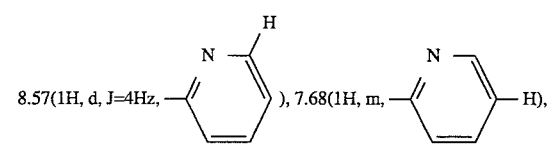

7.36(6H, m, P$\underline{h}$CH$_2$OCO—, 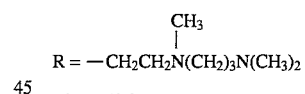), 7.20(1H, m,

), 6.74(1H, s, 5-H), 6.43(1H, s, 8-H), 6.29(2H, s, 2'-H,

6'-H), 5.93, 5.92(2H, d × 2, J=1Hz, —OC$\underline{H}_2$O—), 5.25(2H, s, PhC$\underline{H}_2$OCO—), 4.55(1H, d, J=5Hz, 1-H), 4.10(1H, m, 11α-H), 4.00(1H, m, 11β-H), 3.73(1H, d, J=8.1Hz, —NCH$_2$—), 3.67(6H, s, 3'-OC$\underline{H}_3$, 5'-OC$\underline{H}_3$), 3.15(1H, m, 4-H), 2.97(1H, dd, J=5.3Hz, 9.8Hz, 2-H), 2.87(1H, m, 3-H), 2.44(2H, m, —CH$_2$C$\underline{H}_2$N<), 2.34(3H, s, >NC$\underline{H}_3$), 1.91(1H, m, —C$\underline{H}_2$CH$_2$N<), 1.78(1H, m, —C$\underline{H}_2$CH$_2$N<)

Compound: 27

R = —CH$_2$CH$_2$N(CH$_2$)$_3$N(CH$_3$)$_2$
    |
    CH$_3$

Yield: 58.0%
$^1$H-NMR [Solvent: CDCl$_3$]: δ(ppm)
7.46(5H, m, P$\underline{h}$CH$_2$OCO—), 6.75(1H, s, 5-H), 6.44(1H, s, 8-H), 6.30(2H, s, 2'-H, 6'-H), 5.94(2H, s, —OC$\underline{H}_2$O—), 5.25(2H, s, PhC$\underline{H}_2$OCO—), 4.57(1H, d, J=5Hz, 1-H), 4.35 (1H, t, J=7.7Hz, 11α-H), 4.13(1H, t, J=8.5Hz, 11β-H), 3.68(6H, s, 3'-OC$\underline{H}_3$, 5'-OC$\underline{H}_3$), 3.16(1H, m, 4-H), 3.02 (1H, dd, J=5Hz, 8.5Hz, 2-H), 2.92(1H, m, 3-H), 2.38(6H, m, —C$\underline{H}_2$NC$\underline{H}_2$CH$_2$CH$_2$N(CH$_3$)$_2$), 2.27(6H, s, —N(C$\underline{H}_3$)$_2$), 2.24 (3H, s, —N(C$\underline{H}_3$)—CH$_2$—), 1.68–2.07(4H, m, —C$\underline{H}_2$CH$_2$N—CH$_2$C$\underline{H}_2$CH$_2$N(CH$_3$)$_2$)

EXAMPLE 28

Synthesis of 4-desoxy-4'-demethyl-4-(3-N,N-dimethylamino-1-propyl)-4-epipodophyllotoxin (Compound 28)

To a solution of 230 mg (0.38 mmol) of 4-desoxy-4'-demethyl-4'-O-benzyloxycarbonyl-4-(3-N,N-dimethy-lamino-1-propyl)-4-epipodophyllotoxin, obtained in Example 12, in 4 ml of ethyl acetate-methanol (1:1) was added 50 mg of 10% palladium-on-carbon and the mixture was reacted at room temperature in hydrogen streams at atmospheric pressure for 4 hours. After the catalyst was filtered off, the solvent was distilled off and the residue was purified by column chromatography (silica 5 g, eluent: chloroform-methanol=20:1). The eluate was dissolved in 2 ml of dichloroethane followed by addition of 0.2 ml of 4N-HCl-ethyl acetate. The mixture was concentrated under reduced pressure and the residue was crystallized from diethyl ether to give 110 mg (yield 61.5%) of 4-desoxy-4'-demethyl-4-(3-N,N-dimethylamino-1-propyl)-4-epipodophyllotoxin (Compound 28).

EXAMPLE 29

Synthesis of 4-desoxy-4'-demethyl-4-(2-N,N-diethylamino-1-ethyl)-4-epipodophyllotoxin (Compound 31)

To a solution of 160 mg (0.25 mmol) of 4-desoxy-4'-demethyl-4'-O-benzyloxycarbonyl-4-(2-N,N-diethylamino-1-ethyl)-4-epipodophyllotoxin, obtained in Example 15, in 20 ml of ethyl acetate-methanol (1:1) was added 20 mg of 10% palladium-on-carbon and the mixture was reacted at room temperature in hydrogen streams at atmospheric pressure for 10 hours. After the catalyst was filtered off, the solvent was removed by concentration under reduced pressure and the residue was crystallized from diethyl ether to give 102 mg (yield 84.3%) of 4-desoxy-4'-demethyl-4-(2-N,N-diethylamino-1-ethyl)-4-epipodophyllotoxin (Compound 31).

EXAMPLES 30 THROUGH 53

Compounds 29, 30, 32 though 53, shown in Table 2, were synthesized in the same manner as Examples 28 and 29.

TABLE 2

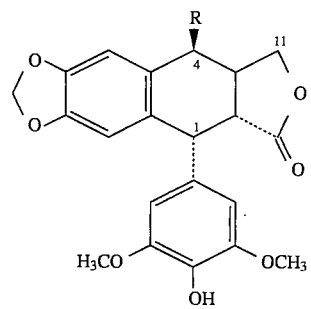

Compound: 28
R = -CH₂CH₂CH₂N(CH₃)₂.HCl
Yield: 61.5%   Melting point: 240–243° C.
¹H-NMR [Solvent: DMSO-d₆]: δ(ppm)
9.74(1H, brs, N⁺H), 8.22(1H, s, 4'-OH), 6.89(1H, s, 5-H), 6.45(1H, s, 8-H), 6.20(2H, s, 2'-H, 6'-H), 5.98 (1H, d, J=1Hz, —OC$\underline{H}_2$O—), 5.96(1H, d, J=1Hz, —OC$\underline{H}_2$O—), 4.43(1H, d, J=5.5Hz, 1-H), 4.38(1H, t, J=8Hz, 11α-H), 4.12(1H, dd, J=11Hz, 8Hz, 11β-H), 3.62(6H, s, 3'-OC$\underline{H}_3$, 5'-OC$\underline{H}_3$), 3.12(1H, dd, J=14.5Hz, 5.5Hz, 2-H), 3.08(2H, m, —C$\underline{H}_2$N<), 3.05(1H, m, 4-H), 2.86(1H, m, 3-H), 2.75 (6H, s, —N(C$\underline{H}_3$)₂), 1.84(1H, m, —CH₂C$\underline{H}_2$CH₂N<), 1.76(1H, m, —CH₂C$\underline{H}_2$CH₂N<), 1.61(1H, m, —C$\underline{H}_2$CH₂CH₂N<), 1.41(1H, m, —CH₂C$\underline{H}_2$CH₂N<)

Compound: 29
R = —CH₂CH₂N(CH₃)₂.HCl
Yield: 81.8%   Melting point: 226–228° C.
¹H-NMR [Solvent: CD₃OD]: δ(ppm)
6.81(1H, s, 5-H), 6.47(1H, s, 8-H), 6.29(2H, s, 2'-H, 6'-H), 5.93(1H, d, J=1.0Hz, —OC$\underline{H}_2$O—), 5.92(1H, d, J=1.0Hz, —OC$\underline{H}_2$O—), 4.56(1H, d, J=5.5Hz, 1-H), 4.42(1H, dd, J=8.5Hz, 7.5Hz, 11α-H), 4.17(1H, dd, J=11Hz, 8.5Hz, 11β-H), 3.71(6H, s, 3'-OC$\underline{H}_3$, 5'-OC$\underline{H}_3$), 3.3(2H, m, TABLE 2-continued

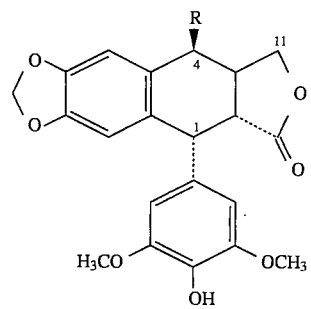

—C$\underline{H}_2$N<), 3.24(1H, m, 4-H), 3.17(1H, dd, J=14.5Hz, 5.5Hz, 2-H), 3.05(1H, m, 3-H), 2.87(6H, s, —N(C$\underline{H}_3$)₂), 2.19(1H, m, —C$\underline{H}_2$CH₂N<), 1.91(1H, m, —C$\underline{H}_2$CH₂N<)

Compound: 30

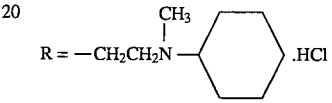

Yield: 81.0%   Melting point: 240–242° C. (decomp.)
¹H-MNR [Solvent: DMSO-d₆]: δ(ppm)
9.94(1H, brs, N⁺H), 8.23(1H, s, 4'-OH), 7.05, 7.02(1H, s, 5-H), 6.46(1H, s, 8-H), 6.20(2H, s, 2'-H, 6'-H), 5.99(1H, d, J=1.0Hz, —OC$\underline{H}_2$O—), 5.97(1H, d, J=1.0Hz, —OC$\underline{H}_2$O—), 4.45(1H, d, J=5.5Hz, 1-H), 4.38(1H, m, 11α-H), 4.15(1H, m, 11β-H), 3.62(6H, s, 3'-OC$\underline{H}_3$, 5'-OC$\underline{H}_3$),

3.12(2H, m, 2-H, 4-H), 2.87(1H, m, 3-H), 2.8(1H, m, —C$\underline{H}_2$N<), 2.65(3H, s, >NC$\underline{H}_3$), 2.27(1H, m, —C$\underline{H}_2$CH₂N<),

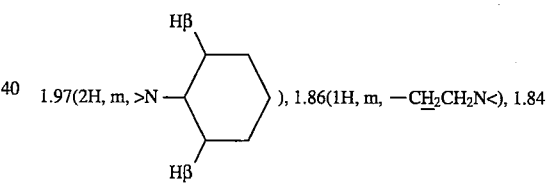

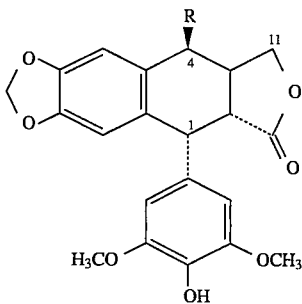

Compound: 31
R = —CH₂CH₂N(C₂H₅)₂
Yield: 84.3%   Melting point: 204–205° C.
¹H-NMR [Solvent: CDCl₃]: δ(ppm)
6.66(1H, s, 5-H), 6.38(1H, s, 8-H), 6.24(2H, s, 2'-H,

TABLE 2-continued

[Structure: naphtho-dioxole fused lactone with R group at position 4 and 3,5-dimethoxy-4-hydroxyphenyl at position 1]

6'-H), 5.87(1H, d, J=1.5Hz, —OC<u>H</u>₂O—), 5.86(1H, d, J=1.5Hz, —OC<u>H</u>₂O—), 5.30(1H, b, 4'-OH), 4.47(1H, d, J=5.0Hz, 1-H), 4.27(1H, dd, J=9.7Hz, 11α-H), 4.05(1H, t, J=9Hz, 11β-H), 3.70(6H, s, 3'-OC<u>H</u>₃, 5'-OC<u>H</u>₃), 3.07 (1H, dt, J=7Hz, 5Hz, 4-H), 2.92(1H, dd, J=14Hz, 5Hz, 2-H), 2.88(1H, dddd, J=14Hz, 9Hz, 7Hz, 5Hz, 3-H), 2.50 (4H, q, J=7Hz, —N(C<u>H</u>₂CH₃)₂), 2.41(2H, m, —C<u>H</u>₂CH₂N<), 1.82(1H, m, —CH₂C<u>H</u>₂N<), 1.64(1H, m, —C<u>H</u>₂CH₂N<), 0.99 (6H, t, J=7Hz, —N(CH₂C<u>H</u>₃)₂)

Compound: 32

R = —CH₂CH₂N(CH₃)CH₂CH₂OH·HCl

Yield: 72.0%  Melting point: 234–237° C. (decomp.)
¹H-NMR [Solvent: CD₃OD]: δ(ppm)
6.83(1H, s, 5-H), 6.47(1H, s, 8-H), 6.29(2H, s, 2'-H, 6'-H), 5.93(1H, d, J=1Hz, —OC<u>H</u>₂O—), 5.92(1H, d, J=1Hz, —OC<u>H</u>₂O—), 4.56(1H, d, J=5.5Hz, 1-H), 4.42(1H, dd, J=8.5Hz, 7.5Hz, 11α-H), 4.14(1H, dd, J=11Hz, 8.5Hz, 11β-H), 3.86(2H, t, J=5.5Hz, >NCH₂C<u>H</u>₂OH), 3.71(6H, s, 3'-OC<u>H</u>₃, 5'-OC<u>H</u>₃), 3.3(2H, m, —C<u>H</u>₂CH₂NCH₂CH₂OH), 3.2–3.3 (3H, m, 4-H, —C<u>H</u>₂CH₂OH), 3.17(1H, dd, J=14.5Hz, 5.5Hz, 2-H), 3.05(1H, m, 3-H), 2.91(3H, s, >NC<u>H</u>₃), 2.23(1H, m, —C<u>H</u>₂CH₂NCH₂CH₂OH), 1.96(1H, m, —C<u>H</u>₂CH₂NCH₂CH₂OH)

Compound: 33

R = —CH₂CH₂N(CH₃)—N(CH₃)₂·HCl

Yield: 89.2%  Melting point: 224–226° C.
¹H-NMR [Solvent: CD₃OD]: δ(ppm)
6.81(1H, s, 5-H), 6.45(1H, s, 8-H), 6.30(2H, s, 2'-H, 6'-H), 5.93(1H, d, J=1Hz, —OC<u>H</u>₂O—), 5.92(1H, d, J=1Hz, —OC<u>H</u>₂O—), 4.55(1H, d, J=5.5Hz, 1-H), 4.43(1H, dd, J=8.5Hz, 7.5Hz, 11α-H), 4.16(1H, dd, J=11Hz, 8.5Hz, 11β-H), 3.71(6H, s, 3'-OC<u>H</u>₃, 5'-OC<u>H</u>₃), 3.3(2H, m, —C<u>H</u>₂N<), 3.24(1H, m, 4-H), 3.15(1H, dd, J=14.5Hz, 5.5Hz, 2-H), 3.02(1H, m, 3-H), 2.80(6H, brs, —N(C<u>H</u>₃)₂), 2.72(3H, brs, —N(C<u>H</u>₃)—N<), 2.13(1H, m, —C<u>H</u>₂CH₂N<), 1.80(1H, m, —C<u>H</u>₂CH₂N<)

Compound: 34

R = —CH₂CH₂—[piperazine]N—CH₃·2HCl

Yield: 66.7%  Melting point: 232–236° C. (decomp.)
¹H-NMR [Solvent: DMSO-d₆]: δ(ppm)
6.91(1H, s, 5-H), 6.43(1H, s, 8-H), 6.23(2H, s, 2'-H, 6'-H), 5.94(1H, d, J=1Hz, —OC<u>H</u>₂O—), 5.93(1H, d, J=1Hz, —OC<u>H</u>₂O—), 4.43(1H, d, J=5.5Hz, 1-H), 4.35(1H, t, J=8Hz, 11α-H), 4.15(1H, dd, J=11Hz, 8Hz, 11β-H), 3.64(6H, s, 3'-OC<u>H</u>₃, 5'-OC<u>H</u>₃), 3.20–3.50(10H, m, —C<u>H</u>₂N[piperazine]N—CH₃),

---

[Structure: naphtho-dioxole fused lactone with R group at position 4 and 3,5-dimethoxy-4-hydroxyphenyl at position 1]

3.16(1H, m, 4-H), 3.08(1H, dd, J=14.5Hz, 5.5Hz, 2-H), 2.88 (1H, m, 3-H), 2.72(3H, s, >NC<u>H</u>₃), 2.17(1H, m, —C<u>H</u>₂CH₂N[piperazine]N—), 1.80(1H, m, —C<u>H</u>₂CH₂N[piperazine]N—)

Compound: 35

R = —CH₂CH₂N(CH₃)CH₂CH₂N(CH₃)₂·2HCl

Yield: 71.7%  Melting point: 203–205° C.
¹H-NMR [Solvent: DMSO-d₆]: δ(ppm)
6.95(1H, s, 5-H), 6.44(1H, s, 8-H), 6.23(2H, s, 2'-H, 6'-H), 5.95(1H, d, J=1Hz, —OC<u>H</u>₂O—), 5.94(1H, d, J=1Hz, —OC<u>H</u>₂O—), 4.44(1H, d, J=5.5Hz, 1-H), 4.36(1H, t, J=8Hz, 11α-H), 4.16(1H, dd, J=11Hz, 8Hz, 11β-H), 3.64(6H, s, 3'-OC<u>H</u>₃, 5'-OC<u>H</u>₃), 3.42(6H, brs, —C<u>H</u>₂NCH₂C<u>H</u>₂N<), 3.17 (1H, m, 4-H), 3.11(1H, dd, J=14Hz, 5.5Hz, 2-H), 2.90(1H, m, 3-H), 2.80(6H, s, —N(C<u>H</u>₃)₂), 2.74(3H, s, >N(C<u>H</u>₃)₂), 2.26(1H, m, —C<u>H</u>₂CH₂N(CH₃)CH₂CH₂N<), 1.89(1H, m, —C<u>H</u>₂CH₂N(CH₃)CH₂CH₂N<)

Compound: 36

R = —CH₂CH₂N[morpholine]O·HCl

Yield: 70.0%  Melting point: 251–253° C.
¹H-NMR [Solvent: DMSO-d₆]: δ(ppm)
10.48(1H, brs, N⁺H), 8.22(1H, brs, 4'-OH), 6.96(1H, s, 5-H), 6.46(1H, s, 8-H), 6.20(2H, s, 2'-H, 6'-H), 5.99(1H, s, —OC<u>H</u>₂O—), 5.97(1H, s, —OC<u>H</u>₂O—), 4.45 (1H, d, J=5.5Hz, 1-H), 4.37(1H, t, J=8Hz, 11α-H), 4.14 (1H, dd, J=11Hz, 8Hz, 11β-H), 3.97(2H, brd, —N[morpholine]O), 3.73 (2H, brt, J=12Hz, —N[morpholine]O), 3,62(6H, s, 3'-OC<u>H</u>₃, 5'-OC<u>H</u>₃),

Hβ

3.45(1H, brd, J=12Hz, —N[morpholine]O),

TABLE 2-continued

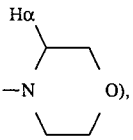

3.40(1H, brd, J=12Hz, Hα −N⟩O), 3.3(1H, m, −CH₂CH₂N⟩O), 3.15(1H, m, 4-H), 3.11(1H, dd, J=14Hz, 5.5Hz, 2-H), 3.06(3H, m, −CH₂CH₂N⟩O), 2.88(1H, m, 3-H), 2.28(1H, m, −CH₂CH₂N⟩O), 1.88(1H, m, −CH₂CH₂N⟩O)

Compound: 37

R = −CH₂CH₂N(CH₃)−N(CH₃)−Ph .HCl

Yield: 67.4%  Melting point: 170–172° C.
¹H-NMR [Solvent: DMSO-d₆]: δ(ppm)
7.17(2H, dd, J=8.5Hz, 7Hz, −N−(Ph)), 7.01(2H, d,
J=8.5Hz, −N−(Ph)), 6.67(1H, t, J=7Hz,
−N−(Ph)−H), 6.66(1H, s, 5-H), 6.39(1H, s, 8-H),
6.18(2H, s, 2'-H, 6'-H), 5.92(1H, s, −OCH₂O−), 5.90(1H, s,
−OCH₂O−), 4.38(1H, d, J=5.5Hz, 1-H), 4.30(1H, t, J=8Hz,
11α-H), 4.02(1H, dd, J=12Hz, 8Hz, 11β-H), 3.61(6H, s, 3'-OCH₃, TABLE 2-continued

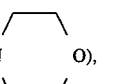

5'-OCH₃), 3.17(1H, m, 4-H), 3.09(1H, dd, J=14.5Hz,
5.5Hz, 2-H), 2.84(1H, m, 3-H), 2.75(3H, s, −N(CH₃)Ph),
2.69(2H, m, −CH₂N(CH₃)−), 2.38(3H, s, −CH₂N(CH₃)−),
1.93(1H, m, −CH₂CH₂N<), 1.53(1H, m, −CH₂CH₂N<)

Compound: 38

R = −CH₂CH₂N(CH₂)₅CH₃.HCl with CH₃ branch

Yield: 66.1%  Melting point: 210–217° C.
¹H-NMR [Solvent: DMSO-d₆]: δ(ppm)
9.73, 9.69(1H, brs, N⁺H), 8.23(1H, s, 4'-OH), 7.00,
6.96(1H, s, 5-H), 6.46(1H, s, 8-H), 6.19(2H, s, 2'-H,
6'-H), 5.99(1H, s, −OCH₂O−), 5.97(1H, s, −OCH₂O−), 4.45
(1H, d, J=5.5Hz, 1-H), 4.36(1H, t, J=8Hz, 11α-H), 4.14,
4.11(1H, dd, J=10Hz, 8Hz, 11β-H), 3.62(6H, s, 3'-OCH₃,
5'-OCH₃), 3.20(1H, m, 4-H), 3.14(1H, dd, J=14.5Hz,
5.5Hz, 2-H), 3.09(1H, brs, −CH₂CH₂N(CH₃)CH₂(CH₂)₄−),
2.96(1H, brs, −CH₂CH₂N(CH₃)CH₂(CH₂)₄−), 2.88(1H, brs,
3-H), 2.73(3H, s, >NCH₃), 2.23(1H, m, −CH₂CH₂N(CH₃)−),
1.82(1H, m, −CH₂CH₂N(CH₃)−), 1.63(2H, brs,
−CH₂CH₂N(CH₃)CH₂CH₂(CH₂)₃−), 1.29(6H, brs,
−N(CH₃)CH₂CH₂(CH₂)₃CH₃),
0.88(3H, t, J=7Hz, >N(CH₂)₅CH₃)

Compound: 39

R = −CH₂CH₂N⟨⟩CH₂OH .HCl

Yield: 59.3%  Melting point: 239–244° C. (decomp.)
¹H-NMR [Solvent: DMSO-d₆]: δ(ppm)
9.63(1H, brs, N⁺H), 8.22(1H, s, 4'-OH), 7.02(1H, s, 5-
H), 6.45(1H, s, 8-H), 6.20(2H, s, 2'-H, 6'-H), 5.99
(1H, s, −OCH₂O−), 5.96(1H, s, −OCH₂O−), 5.44(1H, t,
J=5Hz, −CH₂OH), 4.44(1H, d, J=5Hz, 1-H), 4.35(1H, t,
J=8Hz, 11α-H), 4.13(1H, dd, J=11Hz, 8Hz, 11β-H), 3.77
(1H, m, −CH₂OH), 3.65(1H, m, −CH₂OH), 3.62(6H, s, 3'-

OCH₃, 5'-OCH₃), 3.54(1H, m, −N⟩), 3.54(1H,m,

H CH₂OH

−N⟩Hβ CH₂OH), 3.54(1H, m, −CH₂−N⟩), 3.13(1H, dd,

TABLE 2-continued

[Structure: tetracyclic compound with R group at position 4, positions 1, 11, and methylenedioxy; aryl group with H₃CO, OCH₃ and OH substituents]

J=15Hz, 5Hz, 2-H), 3.13(1H, m, —N⟨Hα/CH₂OH⟩), 3.13(1H, m, 4-H), 3.00(1H, m, —CH₂—N⟨⟩), 2.86(1H, m, 3-H), 2.27

(1H, m, —CH₂CH₂—N⟨⟩), 2.08(1H, m,

—N⟨CH₂OH/Hβ⟩), 1.95(1H, m, —N⟨Hβ/CH₂OH⟩), 1.90(1H, m,

—CH₂CH₂N⟨⟩), 1.86(1H, m, —N⟨Hα/CH₂OH⟩), 1.76(1H, m,

—N⟨⟩/CH₃OH Hα)

Compound: 40

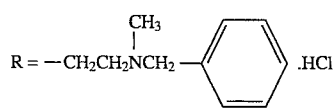

R = —CH₂CH₂N(CH₃)CH₂—C₆H₄ · HCl

Yield: 69.8%  Melting point: 204–205° C.
$^1$H-NMR [Solvent: DMSO-$d_6$]: δ(ppm)
10.76(1H, brs, N⁺H), 7.96(1H, brs, 4'-OH),

TABLE 2-continued

[Structure: same tetracyclic compound with R group]

7.55(2H, brs, —NCH₂—C₆H₄—H), 7.46(3H, brs,

—CH₂—C₆H₄—H), 6.90, 6.86(1H, s, 5-H), 6.45(1H, s,

8-H), 6.22(2H, s, 2'-H, 6'-H), 5.98(1H, d, J=1Hz,
—OCH₂O—), 5.96(1H, d, J=1Hz, —OCH₂O—), 4.45

(1H, d, J=5.5Hz, 1-H), 4.39(1H, brs, —CH₂—C₆H₅), 4.31(1H, m, 11α-H), 4.22(1H, brs, —CH₂—C₆H₅), 4.11(1H, brt, J=8.5Hz, 11β-H), 3.64(6H, s, 3'-OCH₃, 5'
—OCH₃), 3.10(1H, over lapped, 2-H), 2.89(1H, m, 3-H),
2.67(3H, brs, >NCH₃), 2.33(1H, m, —CH₂CH₂N<), 1.96(1H,
m, —CH₂CH₂N<)

Compound: 41

R = —CH₂CH₂NCH(CH₂OH)₂ · HCl, with CH₃ on N

Yield: 67.0%  Melting point: 222–225° C.
$^1$H-NMR [Solvent: DMSO-$d_6$]: δ(ppm)
9.29(1H, brs, N⁺H), 7.96(1H, brs, 4'-OH), 6.95(1H, s,
5-H), 6.45(1H, s, 8-H), 6.23(2H, s, 2'-H, 6'-H), 5.97
(1H, d, J=1Hz, —OCH₂O—), 5.96(1H, d, J=1Hz, —OCH₂O—),
5.24(2H, brs, —CH(CH₂OH)₂), 4.45(1H, d, J=5.5Hz, 1-H),
4.36(1H, t, J=8Hz, 11α-H), 4.17(1H, dd, J=11Hz, 8Hz,
11β-H), 3.73(4H, brs, —CH(CH₂OH)₂), 3.64(6H, s, 3'-
OCH₃, 5'-OCH₃), 3.2–3.5(2H, m, —CH₂CH₂N<), 3.39(1H,
brs, —CH(CH₂OH)₂), 3.15(1H, m, 4-H), 3.09(1H, over
lapped, 2-H), 2.89(1H, m, 3-H), 2.81(3H, brs, >NCH₃),
2.28(1H, m, —CH₂CH₂N<), 1.91(1H, m, —CH₂CH₂N<)

Compound: 42

R = —CH₂CH₂NCH₂CH₂N⟨piperidine⟩ · 2HCl, with CH₃ on first N

TABLE 2-continued

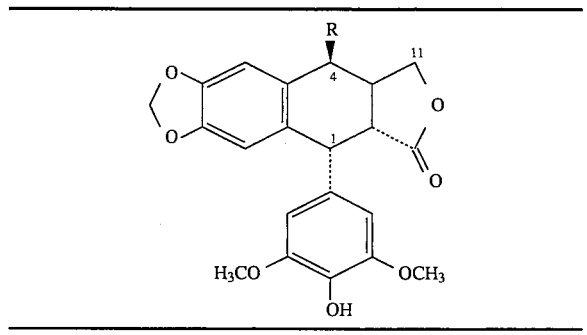

Yield: 66.0%  Melting point: 210–216° C.
¹H-NMR [Solvent: DMSO-d₆]: δ(ppm)
11.30(1H, brs, N⁺H), 10.78(1H, brs, N⁺H), 8.23(1H, brs, 4'-OH), 7.00(1H, brs, 5-H), 6.46(1H, s, 8-H), 6.20 (2H, s, 2'-H, 6'-H), 5.99(1H, s, —OC$\underline{H}_2$O—), 5.97(1H, s, —OC$\underline{H}_2$O—), 4.45(1H, d, J=5.5Hz, 1-H), 4.37(1H, t, J=8Hz, 11α-H), 4.15(1H, m, 11β-H), 3.62(6H, s, 3'-OC$\underline{H}_3$, 5'-OC$\underline{H}_3$), 3.16(1H, m, 4-H), 3.14(1H, dd, J=14.5Hz, 5.5Hz, 2-H), 3.0–4.1(2H, over lapped, 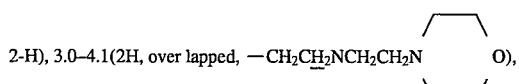

3.0–4.1(12H, 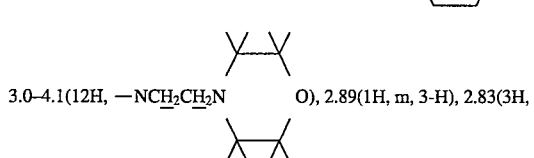 ), 2.89(1H, m, 3-H), 2.83(3H, brs, >NC$\underline{H}_3$), 2.30(1H, m, 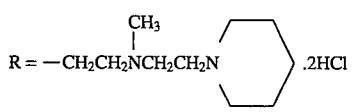

Compound: 43

R = 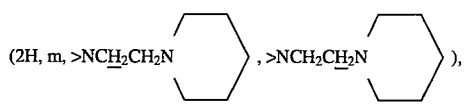 .2HCl

Yield: 69.0%  Melting point: 210–213° C.
¹H-NMR [Solvent: DMSO-d₆]: δ(ppm)
10.41(1H, brs, N⁺H), 10.72, 10.66(1H, brs, N⁺H), 8.24 (1H, brs, 4'-OH), 7.03, 6.97(1H, s, 5-H), 6.47(1H, s, 8-H), 6.20(2H, s, 2'-H, 6'-H), 5.99(1H, s, —OC$\underline{H}_2$O—), 5.97(1H, s, —OC$\underline{H}_2$O—), 4.45(1H, d, J=5.5Hz, 1-H), 4.37 (1H, t, J=7.5Hz, 11α-H), 4.17, 4.13(1H, m, 11β-H), 3.63

(2H, m, 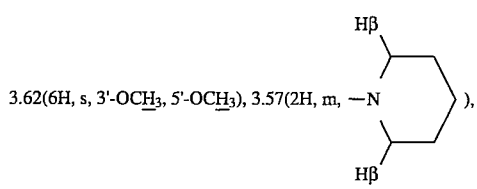 ), 3.62(6H, s, 3'-OC$\underline{H}_3$, 5'-OC$\underline{H}_3$), 3.57(2H, m, 3.50(2H, m, >NC$\underline{H}_2$CH$_2$N ⌬ , >NCH$_2$C$\underline{H}_2$N ⌬ ), 3.45(1H, m, 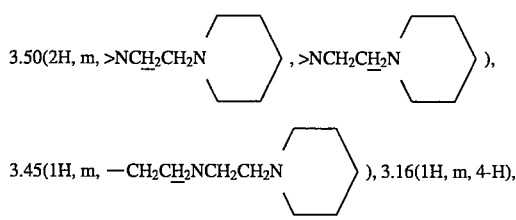 ), 3.16(1H, m, 4-H), 3.14(1H, dd, J=14.5Hz, 5.5Hz, 2-H), 3.08(1H, m,

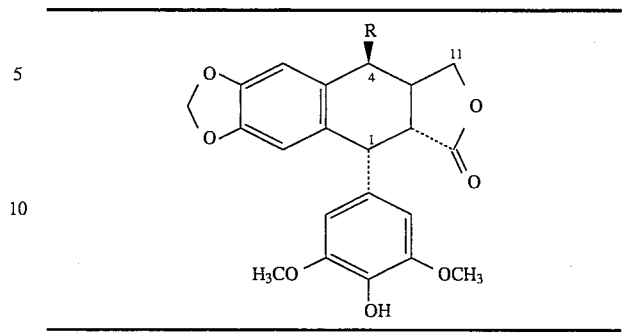

2.90(1H, m, 3-H), 2.84(3H, brs, >NC$\underline{H}_3$), 2.30(1H, m, —C$\underline{H}_2$CH$_2$N<), 1.90(1H, m, —C$\underline{H}_2$CH$_2$N<), 1.7–1.9(5H, m,

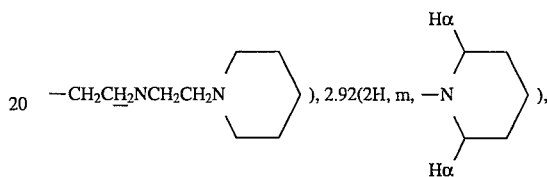

Compound: 44

R = 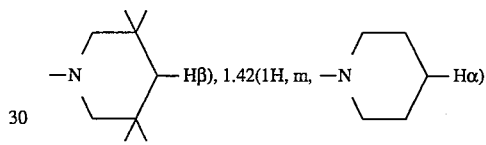 .HCl

Yield: 61.0%  Melting point: 250–252° C.
¹H-NMR [Solvent: DMSO-d₆]: δ(ppm)
9.48(1H, brs, N⁺H), 8.23(1H, s, 4'-OH), 6.96(1H, s, 5-H), 6.46(1H, s, 8-H), 6.19(2H, s, 2'-H, 6'-H), 4.45 (1H, d, J=5.5Hz, 1-H), 4.37(1H, t, J=8Hz, 11α-H), 4.12 (1H, dd, J=11Hz, 8Hz, 11β-H), 3.62(6H, s, 3'-OC$\underline{H}_3$, 5'-OC$\underline{H}_3$), 3.44(2H, m, 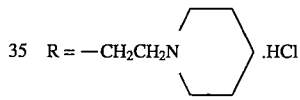 ), 3.26(1H, m,

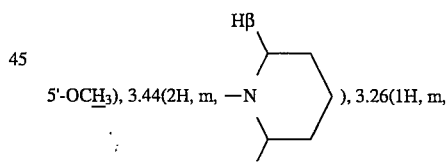 ), 3.13(1H, dd, J=14.5Hz, 5.5Hz, 2-H), 3.13(1H, m, 4-H), 2.97(1H, m, —C$\underline{H}_2$CH$_2$N ⌬ ), 2.89(1H, m, 3-H), 2.86(2H, m, 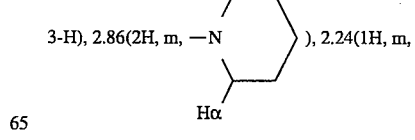 ), 2.24(1H, m, TABLE 2-continued

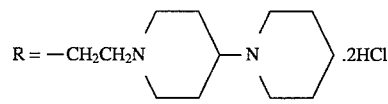

—CH₂CH₂N⟨piperidine⟩), 1.85(1H, m, —CH₂CH₂N⟨piperidine⟩), 1.79(2H, m, —N⟨Hβ/Hβ⟩), 1.68(2H, m, —N⟨Hα/Hα⟩), 1.68(1H, m, —N⟨piperidine⟩—Hβ), 1.38(1H, m, —N⟨piperidine⟩—Hα)

Compound: 45

R = —CH₂CH₂N⟨piperidine⟩—N⟨piperidine⟩ .2HCl

Yield: 65.4% Melting point: 280° C. (decomp.)
¹H-NMR [Solvent: DMSO-d₆ + D₂O(2:1)]: δ(ppm)
6.87(1H, s, 5-H), 6.49(1H, s, 8-H), 6.25(2H, s, 2'-H, 6'-H), 5.95(2H, s, —OCH₂O—), 4.51(1H, d, J=5.5Hz, 1-H), 4.44(1H, t, J=8Hz, 11α-H), 4.13(1H, dd, J=11Hz, 8Hz, 11β-H), 3.68(2H, m, —N⟨Hβ/Hβ⟩—N⟨Hβ/Hβ⟩), 3.65(6H, s, 3'-OCH₃, 5'-OCH₃), 3.43(3H, m,

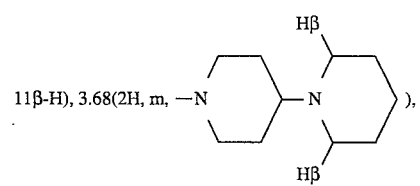

), 3.1–3.3(2H, over lapped,

—CH₂CH₂N⟨piperidine⟩), 3.1–3.3(1H, over lapped, 4-H), 3.18(1H, dd, J=15Hz, 5.5Hz, 2-H), 2.4–3.1(5H, over lapped, 3-H, TABLE 2-continued

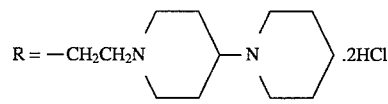

—N⟨Hα/Hα⟩—N⟨piperidine⟩, —N⟨Hα/Hα⟩—N⟨piperidine⟩), 2.30(2H, m, —N⟨Hβ/Hβ⟩—N⟨piperidine⟩), 2.17(1H, m, —CH₂CH₂N⟨piperidine⟩), 1.8–2.0(5H, over lapped,

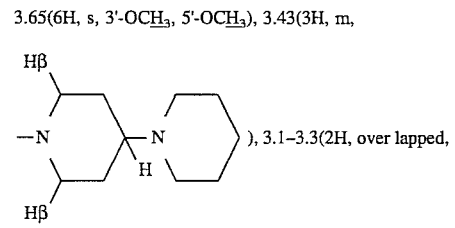

—CH₂CH₂N⟨Hα/Hα⟩—N⟨Hβ/Hβ⟩), 1.6–1.8(3H, over lapped,

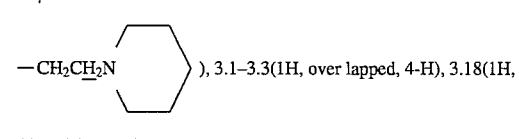

—N⟨piperidine⟩—N⟨Hα/Hα⟩—Hβ), 1.43(1H, m, —N⟨piperidine⟩—Hα)

Compound: 46

R = —CH₂CH₂N(CH₃)CH₂CH₂OCH₃ . HCl

Yield: 92.0% Melting point: 193–195° C.
¹H-NMR [Solvent: DMSO-d₆]: δ(ppm)
8.26(1H, s, 4'-OH), 6.97(1H, d, J=7.9Hz, 5-H), 6.46(1H, s, 8-H), 6.20(2H, s, 2'-H, 6'-H), 5.99 (1H, s, —OCH₂O—), 5.97(1H, s, —OCH₂O—), 4.45(1H, d, J=5.6Hz, 1-H), 4.36(1H, t, J=7.2Hz, 11α-H), 4.17(1H, m, 11β-H), 3.69(2H, m, —CH₂OCH₃), 3.62(6H, s, 3'-OCH₃, 5'-OCH₃), 3.30(3H, s, —CH₂OCH₃), 2.82–3.39(7H, m, 2-H, 3-H, 4-H, —CH₂NCH₂—), 2.76(3H, s, >NCH₃), 2.29(1H, m, —CH₂CH₂N<), 1.86(1H, m, —CH₂CH₂N<)

Compound: 47

R = —CH₂CH₂N(CH₃)CH₂CH₂N(C₂H₅)₂ . 2HCl

Yield: 41.5% Melting point: 195–197° C.

TABLE 2-continued

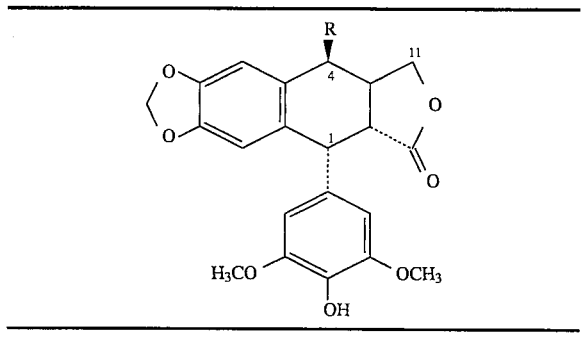

$^1$H-NMR [Solvent: DMSO-d$_6$]: δ(ppm)
11.37(1H, br, N$^+$H), 11.17(1H, br, N$^+$H), 8.20(1H, br, 4'-OH), 7.05, 7.00(1H, s, 5-H), 6.45(1H, s, 8-H), 6.19 (2H, s, 2'-H, 6'-H), 5.99(1H, s, —OCH$_2$O—), 5.96(1H, s, —OCH$_2$O—), 4.45(1H, d, J=5.6Hz, 1-H), 4.37(1H, t, J=7.2Hz, 11α-H), 4.10–4.30(1H, m, 11β-H), 3.61(6H, s, 3'-OCH$_3$, 5'-OCH$_3$), 3.00–3.60(12H, m, 2-H, 4-H, —CH$_2$NCH$_2$CH$_2$N(CH$_2$CH$_3$)$_2$), 2.90(1H, m, 3-H), 2.81(2H, s, >NCH$_3$), 2.32(1H, m, —CH$_2$CH$_2$N<), 1.91(1H, m, —CH$_2$CH$_2$N<), 1.26(6H, t, —N(CH$_2$CH$_3$)$_2$)

Compound: 48

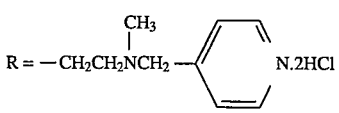

Yield: 31.0%  Melting point: 181–183° C.
$^1$H-NMR [Solvent: DMSO-d$_6$]: δ(ppm)

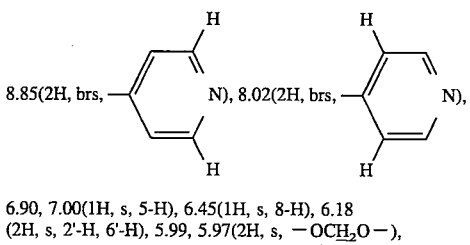

6.90, 7.00(1H, s, 5-H), 6.45(1H, s, 8-H), 6.18 (2H, s, 2'-H, 6'-H), 5.99, 5.97(2H, s, —OCH$_2$O—), 4.10–4.70(5H, m, 1-H, —N(CH$_3$)CH$_2$— N, 11-H), 3.61(6H, s, 3'-OCH$_3$, 5'-OCH$_3$), 3.00–4.00(4H, m, —CH$_2$CH$_2$N<, 2-H, 4-H), 2.90(1H, m, 3-H), 2.67(3H, s, >NCH$_3$), 2.40(1H, m, —CH$_2$CH$_2$N<), 2.00(1H, m, —CH$_2$CH$_2$N<)

Compound: 49

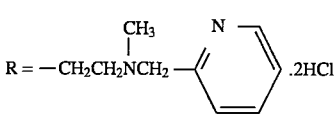

Yield: 57.0%  Melting point: 185–186° C.
$^1$H-NMR [Solvent: DMSO-d$_6$]: δ(ppm)

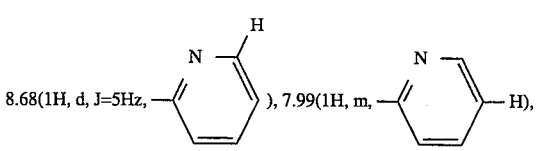

TABLE 2-continued

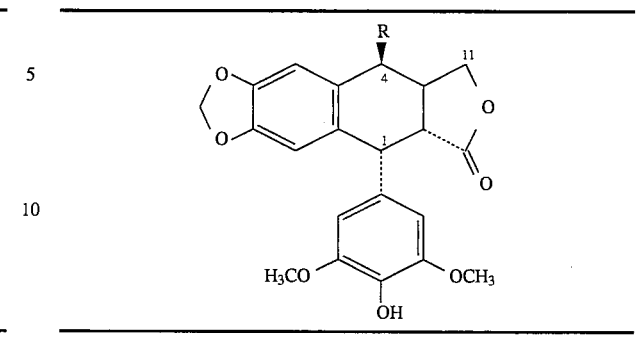

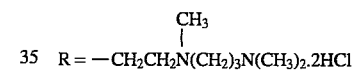

6.95(1H, s, 5-H), 6.44(1H, s, 8-H), 6.19(2H, s, 2'-H, 6'-H), 5.99, 5.97(2H, s × 2, —OCH$_2$O—), 4.50(2H, s,

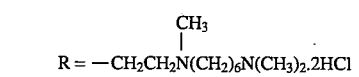

J=7.9Hz, 11α-H), 4.17(1H, m, 11β-H), 3.62(6H, s, 3'-OCH$_3$, 5'-OCH$_3$), 3.11–3.40(4H, m, 2-H, 4-H, —CH$_2$CH$_2$N<), 2.89(1H, m, 3-H), 2.76(3H, s, >NCH$_3$), 2.40(1H, m, —CH$_2$CH$_2$N<), 1.99(1H, m, —CH$_2$CH$_2$N<)

Compound: 50

R = —CH$_2$CH$_2$N(CH$_2$)$_3$N(CH$_3$)$_2$.2HCl
        |
        CH$_3$

Yield: 92.0%  Melting point: 238° C. (decomp.)
$^1$H-NMR [Solvent: DMSO-d$_6$]: δ(ppm)
8.26(1H, s, 4'-OH), 7.03(1H, s, 5-H), 6.45 (1H, s, 8-H), 6.19(2H, s, 2'-H, 6'-H), 5.99, 5.97 (2H, s × 2, —OCH$_2$O—), 4.44(1H, d, J=5.2Hz, 1-H), 4.37(1H, m, 11α-H), 4.34(1H, m, 11β-H), 3.62(6H, s, 3'-OCH$_3$, 5'-OCH$_3$), 2.90–3.40(9H, m, 2-H, 3-H, 4-H, —CH$_2$NCH$_2$CH$_2$CH$_2$N<), 2.75(9H, m, —N(CH$_3$)—(CH$_2$)$_3$N(CH$_3$)$_2$), 1.91–2.34(4H, m, —CH$_2$CH$_2$NCH$_2$CH$_2$CH$_2$N<)

Compound: 51

R = —CH$_2$CH$_2$N(CH$_2$)$_6$N(CH$_3$)$_2$.2HCl
        |
        CH$_3$

Yield: 75.0%  Melting point: 198–199° C.
$^1$H-NMR [Solvent: DMSO-d$_6$]: δ(ppm)
11.0(2H, br, N$^+$H), 8.26(1H, s, 4'-OH), 7.05 (1H, s, 5-H), 6.44(1H, s, 8-H), 6.19(2H, s, 2'-H, 6'-H), 5.99(2H, s, —OCH$_2$O—), 4.18–4.43(3H, m, 1-H, 11α-H, 11β-H), 3.62(6H, s, 3'-OCH$_3$, 5'-OCH$_3$), 2.51–3.62(9H, m, 2-H, 3-H, 4-H, —CH$_2$NCH$_2$(CH$_2$)$_4$CH$_2$N<), 2.75(6H, s, —N(CH$_3$)$_2$), 2.27(1H, m, —CH$_2$CH$_2$N(CH$_2$)$_6$N<), 1.85(1H, m, —CH$_2$CH$_2$(CH$_2$)$_6$N<), 1.65, 1.33(8H, m, —NCH$_2$(CH$_2$)$_4$CH$_2$N<)

Compound: 52
R = —CH$_2$CH$_2$NHCH$_2$CH$_2$N(CH$_3$)$_2$.2HCl
Yield: 55.0%  Melting point: 213° C. (decomp.)
$^1$H-NMR [Solvent: CDCl$_3$ + CD$_3$OD]: δ(ppm)
6.80(1H, s, 5-H), 6.47(1H, s, 8-H), 6.27(2H, s, 2'-H, 6'-H), 5.95(1H, d, J=1Hz, —OCH$_2$O—), 5.94(1H, d, J=1Hz, —OCH$_2$O—), 4.55(1H, d, J=4.5Hz, 1-H), 4.41(1H, m, 11α-H), 4.26(1H, m, 11β-H), 3.76(6H, s, 3'-OCH$_3$, 5'-OCH$_3$), 3.61(2H, brt, J=6Hz, —NHCH$_2$CH$_2$N<), 3.47(2H, brt, —NHCH$_2$CH$_2$N<), 3.27(1H, m, 4-H), 3.15(2H, m,

TABLE 2-continued

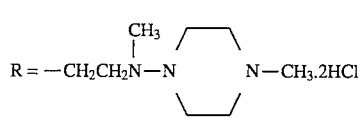

| |
|---|
| —CH₂NHCH₂CH₂N<), 3.05(2H, over lapped, 2-H, 3-H), 2.96(6H, s, —N(CH₃)₂), 2.27(1H, m, —CH₂CH₂NHCH₂CH₂N<), 2.04(1H, m, —CH₂CH₂NHCH₂CH₂N<) |

Compound: 53

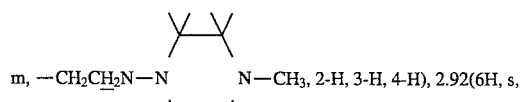

Yield: 67.0% Melting point: 188–190° C.
¹H-NMR [Solvent: DMSO-d₆]: δ(ppm)
13.00(2H, br, N⁺H), 10.94(1H, br, 4'-OH), 7.05(1H, s, 5-H), 6.44(1H, s, 8-H), 6.19(2H, s, 2'-H, 6'-H), 5.98 (2H, s, —OCH₂O—), 4.45(2H, m, 1-H, 11α-H), 4.12(1H, m, 11β-H), 3.61(6H, s, 3'-OCH₃, 5'-OCH₃), 2.20–3.60(13H, m, —CH₂CH₂N—N  N—CH₃, 2-H, 3-H, 4-H), 2.92(6H, s,

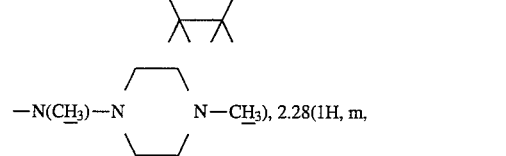

—N(CH₃)—N  N—CH₃), 2.28(1H, m,

—CH₂CH₂N(CH₃)—), 2.04(1H, m, —CH₂CH₂N(CH₃)—)

Pharmacological Test 1

A 96-well plate was inoculated with 1×10³ cells/well of P388 mouse leukemia cell line and incubated for 24 hours. The test compound was dissolved in dimethylformamide and the solution was diluted with medium to various concentrations and added to respective wells. The plate was further incubated for 3 days, after which it was fixed with glutaraldehyde and stained with crystal violet for cytometry. The cytocidal effect of each compound was expressed as the concentration causing a 50% decrease in cell count ($ED_{50}$) as compared with the control. The results are shown in Table 3.

TABLE 3

| Compound No. | $ED_{50}$ (M) |
|---|---|
| 3 | $4.5 \times 10^{-7}$ |
| 5 | $1.2 \times 10^{-7}$ |
| 28 | $1.2 \times 10^{-8}$ |
| 33 | $2.0 \times 10^{-8}$ |
| 34 | $3.0 \times 10^{-9}$ |
| 35 | $1.0 \times 10^{-9}$ |
| 38 | $1.9 \times 10^{-8}$ |
| 43 | $4.1 \times 10^{-9}$ |

TABLE 3-continued

| Compound No. | $ED_{50}$ (M) |
|---|---|
| 44 | $1.2 \times 10^{-8}$ |
| 45 | $3.3 \times 10^{-9}$ |
| 47 | $6.3 \times 10^{-9}$ |
| 52 | $4.0 \times 10^{-8}$ |
| 53 | $4.3 \times 10^{-9}$ |

Pharmacological Test 2

L1210 mouse leukemia cell line, 1×10⁵ cells/mouse, was intraperitoneally transplanted into 7-weeks-old male CDF₁ mice (6 per group). The test compound, in the varying amounts shown below in Table 4, was dissolved in physiological saline containing 3.5% of dimethyl sulfoxide and 6.5% of Tween 80 and the solution was intraperitoneally administered for 5 days following the transplantation of cells for a total of 5 times. The percent life-prolonging effect of the compound was determined by comparison with a group given physiological saline containing 3.5% of dimethyl sulfoxide and 6.5% of Tween 80 only. The results are shown in Table 4.

TABLE 4

| Compound No. | Dosage (mg/kg/day) | Life-prolonging effect (%) |
|---|---|---|
| 36 | 10 | 81 |
| 43 | 5 | 257 |
| 45 | 2.5 | 231 |

Preparation Examples using the compound of the invention are presented below.

Preparation Example 1 Tablets

According to the following formula, tablets were prepared by the established pharmaceutical procedure.

| | |
|---|---|
| Compound 34 | 100 mg |
| Lactose | 47 mg |
| Corn starch | 50 mg |
| Crystalline cellulose | 50 mg |
| Hydroxypropylcellulose | 15 mg |
| Talc | 2 mg |
| Magnesium stearate | 2 mg |
| Ethylcellulose | 30 mg |
| Unsaturated fatty acid glyceride | 2 mg |
| Titanium dioxide | 2 mg |
| Per Tablet | 300 mg |

Preparation Example 2 Granules

According to the following formula, granules were prepared by the established pharmaceutical procedure.

| | |
|---|---|
| Compound 35 | 200 mg |
| Mannitol | 540 mg |
| Corn starch | 100 mg |
| Crystalline cellulose | 100 mg |
| Hydroxypropylcellulose | 50 mg |
| Talc | 10 mg |
| Per wrapper | 1,000 mg |

Preparation Example 3 Fine Granules

According to the following formula, fine granules were prepared by the established pharmaceutical procedure.

| | |
|---|---|
| Compound 43 | 200 mg |
| Mannitol | 520 mg |
| Corn starch | 100 mg |
| Crystalline cellulose | 100 mg |
| Hydroxypropylcellulose | 70 mg |
| Talc | 10 mg |
| Per Wrapper | 1,000 mg |

Preparation Example 4 Capsules

According to the following formula, capsules were prepared by the established pharmaceutical procedure.

| | |
|---|---|
| Compound 45 | 100 mg |
| Lactose | 50 mg |
| Corn starch | 47 mg |
| Crystalline cellulose | 50 mg |
| Talc | 2 mg |
| Magnesium stearate | 1 mg |
| Per capsule | 250 mg |

Preparation Example 5 Injections

According to the following formula, injections were prepared by the established pharmaceutical procedure.

| | |
|---|---|
| Compound 47 | 100 mg |
| Distilled water for injections | q.s. |
| Per ampule | 2 ml |

Preparation Example 6 Suppositories

According to the following formula, suppositories were prepared by the established pharmaceutical procedure.

| | |
|---|---|
| Compound 53 | 100 mg |
| Witepsol S-55 | 1,400 mg |
| (a mixture of mono-, di- and triglycerides of saturated fatty acids from laurid acid to stearic acid, product of Dynamite Nobel) | |
| Per suppository | 1,500 mg |

We claim:

1. A 4-desoxy-4-epipodophyllotoxin derivative of the general formula:

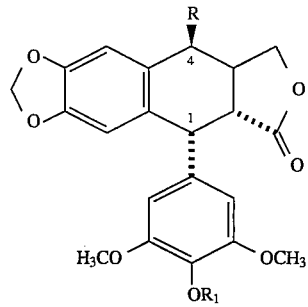

(I)

wherein $R_1$ is a hydrogen atom, R is a group of the formula $-(CH_2)_n NR_2 R_3$ where n is an integer of 1 to 4; $R_2$ is a group of the formula $-N(Ra)(Rb)$ where Ra and Rb combine to form a lower alkyl-substituted piperazino group and $R_3$ is or a lower alkyl group which may be substituted by piperidino; or $R_2$ and $R_3$ combine to form a cyclic structure which may optionally include additional nitrogen atoms and may further have a lower alkyl group or piperidino group, as a substituent, or a pharmaceutically acceptable salt thereof.

2. The 4-desoxy-4-epipodophyllotoxin derivative or a pharmaceutically acceptable salt thereof according to claim 1 wherein n is 2 or 3.

3. The 4-desoxy-4-epipodophyllotoxin derivative or a pharmaceutically acceptable salt thereof according to claim 1 wherein n is 2.

* * * * *